(12) United States Patent
Armitstead et al.

(10) Patent No.: US 11,291,787 B2
(45) Date of Patent: Apr. 5, 2022

(54) METHODS AND APPARATUS FOR TREATMENT OF RESPIRATORY DISORDERS

(71) Applicant: ResMed Pty Ltd, Bella Vista (AU)

(72) Inventors: Jeffrey Peter Armitstead, Sydney (AU); David John Bassin, Sydney (AU); Peter Edward Bateman, Sydney (AU); Gordon Joseph Malouf, Sydney (AU); Dinesh Ramanan, Sydney (AU)

(73) Assignee: ResMed Pty Ltd

( * ) Notice: Subject to any disclaimer, the term of this patent is extended or adjusted under 35 U.S.C. 154(b) by 734 days.

(21) Appl. No.: 15/315,447

(22) PCT Filed: Jun. 10, 2015

(86) PCT No.: PCT/AU2015/050317
§ 371 (c)(1),
(2) Date: Dec. 1, 2016

(87) PCT Pub. No.: WO2015/188227
PCT Pub. Date: Dec. 17, 2015

(65) Prior Publication Data
US 2017/0361044 A1    Dec. 21, 2017

(30) Foreign Application Priority Data
Jun. 10, 2014  (AU) ................. 2014902201

(51) Int. Cl.
*A61M 16/00* (2006.01)
*A61M 16/12* (2006.01)
(Continued)

(52) U.S. Cl.
CPC .... *A61M 16/0069* (2014.02); *A61M 16/0051* (2013.01); *A61M 16/026* (2017.08);
(Continued)

(58) Field of Classification Search
CPC .............. A61M 16/00; A61M 16/0051; A61M 16/0069; A61M 16/021; A61M 16/022;
(Continued)

(56) References Cited

U.S. PATENT DOCUMENTS 4,686,975 A * 8/1987 Naimon ............ A61M 16/0677
128/204.23
4,944,310 A    7/1990 Sullivan
(Continued)

FOREIGN PATENT DOCUMENTS

WO    2004078246 A1    9/2004
WO    2005051469 A1    6/2005
(Continued)

OTHER PUBLICATIONS

International Search Report and Written Opinion for Application No. PCTAU2015/050317 dated Aug. 17, 2015.

*Primary Examiner* — Colin W Stuart
*Assistant Examiner* — Matthew D Ziegler
(74) *Attorney, Agent, or Firm* — Botos Churchill IP Law LLP

(57) ABSTRACT

Methods and apparatus for treating a respiratory disorder, in one aspect, include an apparatus that delivers backup breaths at a sustained timed backup rate that is a function of the patient's spontaneous respiratory rate. Other aspects include apparatus that delivers backup breaths at a rate that gradually increases from a spontaneous backup rate to a sustained timed backup rate or, alternatively, apparatus that oscillates a treatment pressure in antiphase with the patient's spontaneous respiratory efforts when a measure indicative of ventilation is greater than a threshold. Other aspects include apparatus configured to treat Cheyne-Stokes respiration by computing the treatment pressure so as to bring a measure indicative of ventilation of the patient towards a target ventilation that is dependent on the measure indicative of (Continued)

ventilation or, alternatively, by periodically elevating the treatment pressure to a high level for a short time.

34 Claims, 15 Drawing Sheets

(51) Int. Cl.
*A61M 16/16* (2006.01)
*A61M 16/06* (2006.01)
*A61M 16/10* (2006.01)

(52) U.S. Cl.
CPC ...... *A61M 16/0633* (2014.02); *A61M 16/107* (2014.02); *A61M 16/12* (2013.01); *A61M 16/16* (2013.01); *A61M 2016/0018* (2013.01); *A61M 2016/0027* (2013.01); *A61M 2016/0036* (2013.01); *A61M 2202/0208* (2013.01); *A61M 2205/21* (2013.01); *A61M 2205/3592* (2013.01); *A61M 2205/42* (2013.01); *A61M 2205/505* (2013.01)

(58) Field of Classification Search
CPC .............. A61M 16/024; A61M 16/026; A61M 16/0633; A61M 16/10; A61M 16/1005; A61M 16/107; A61M 16/12; A61M 16/14; A61M 2016/0015; A61M 2016/0018; A61M 2016/0027; A61M 2016/003; A61M 2016/0033; A61M 2016/0036; A61M 2016/102; A61M 2202/0208; A61M 2205/21; A61M 2205/33; A61M 2205/3327; A61M 2205/3331; A61M 2205/3334; A61M 2205/3341; A61M 2205/3592; A61M 2205/42; A61M 2205/50; A61M 2205/505; A61M 2230/005; A61M 2230/40; A61M 2230/42; A61B 5/08; A61B 5/0816; A61B 5/0826; A61B 5/087; A61B 5/0871; A61B 2560/0266
See application file for complete search history.

(56) References Cited

U.S. PATENT DOCUMENTS

| | | | |
|---|---|---|---|
| 5,385,142 A | 1/1995 | Brady et al. | |
| 5,551,419 A * | 9/1996 | Froehlich | A61M 16/024 128/204.23 |
| 6,532,959 B1 | 3/2003 | Berthon-Jones | |
| 10,137,266 B2 * | 11/2018 | Shelly | A61M 16/024 |
| 2006/0037615 A1 * | 2/2006 | Wilkinson | A61B 5/08 128/204.23 |
| 2006/0264762 A1 | 11/2006 | Starr | |
| 2007/0215146 A1 * | 9/2007 | Douglas | A61M 16/0051 128/200.24 |
| 2009/0050154 A1 * | 2/2009 | Strothmann | A61M 16/0051 128/204.23 |
| 2009/0050155 A1 * | 2/2009 | Alder | A61B 5/087 128/204.23 |
| 2009/0308394 A1 | 12/2009 | Levi | |
| 2010/0016694 A1 * | 1/2010 | Martin | A61M 16/0051 600/324 |
| 2010/0108066 A1 * | 5/2010 | Martin | A61M 16/026 128/204.23 |
| 2010/0137730 A1 * | 6/2010 | Hatlestad | A61B 5/08 600/529 |
| 2011/0303223 A1 | 12/2011 | Kane et al. | |
| 2012/0012110 A1 * | 1/2012 | Bassin | A61M 16/0066 128/204.23 |
| 2012/0190998 A1 * | 7/2012 | Armitstead | A61B 5/0826 600/534 |
| 2012/0199126 A1 * | 8/2012 | Famugia | A61M 16/024 128/204.23 |
| 2012/0247471 A1 * | 10/2012 | Masic | A61M 16/0051 128/204.23 |
| 2013/0047989 A1 | 2/2013 | Vandine et al. | |
| 2013/0228182 A1 | 9/2013 | Bassin | |

FOREIGN PATENT DOCUMENTS

| | | | | |
|---|---|---|---|---|
| WO | WO-2005051470 A1 * | 6/2005 | | A61B 5/087 |
| WO | 2006024107 A1 | 3/2006 | | |
| WO | WO-2008138040 A1 * | 11/2008 | | A61M 16/0069 |
| WO | WO-2010121290 A1 * | 10/2010 | | A61B 5/14551 |
| WO | 2012128674 A1 | 9/2012 | | |
| WO | WO-2012126041 A1 * | 9/2012 | | A61B 5/083 |
| WO | WO-2013067580 A1 * | 5/2013 | | A61M 16/0051 |
| WO | WO-2013163687 A1 * | 11/2013 | | A61M 16/12 |

* cited by examiner

METHODS AND APPARATUS FOR TREATMENT OF RESPIRATORY DISORDERS

1 CROSS-REFERENCE TO RELATED APPLICATIONS

The present application is a national phase entry under 35 U.S.C. § 371 of International Application No. PCT/AU2015/050317 filed Jun. 10, 2015, published in English, which claims priority from Australian Patent Application No. 2014902201 filed Jun. 10, 2014, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE INVENTION

5.1 Field of The Invention

The present technology relates to one or more of the detection, diagnosis, treatment, prevention and amelioration of respiratory-related disorders. In particular, the present technology relates to medical devices or apparatus, and their use.

5.2 Description of the Related Art

5.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition, published 2011.

A range of respiratory disorders exist. Certain disorders may be characterized by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. OSA results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is an instability disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterized by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterized by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterized by muscle impairment that worsens over years and only mildly reduces life expectancy (e.g. Limb girdle, Facioscapulohumeral and Myotonic muscular dystrophy). Symptoms of respiratory failure in NMD include: increasing generalized weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterized by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising.

5.2.2 Therapies

Nasal Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion by pushing the soft palate and tongue forward and away from the posterior oropharyngeal wall.

Non-invasive ventilation (NIV) therapy provides ventilatory support to a patient through the upper airways to assist the patient in taking a full breath and/or maintaining adequate oxygen levels in the body by doing some or all of the work of breathing. NIV is provided via a non-invasive patient interface. NIV has been used to treat CSR, OHS, COPD, NMD, and Chest Wall disorders.

5.2.3 Diagnosis and Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

5.2.3.1 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH$_2$O. For other forms of therapy, such as the delivery of oxygen, the patient interface may not include a seal sufficient to facilitate delivery to the airways of a supply of air at a positive pressure of about 10 cmH$_2$O.

5.2.3.2 Respiratory Pressure Therapy (RPT) Devices

Air pressure generators are known in a range of applications, e.g. industrial-scale ventilation systems. However, air pressure generators for medical applications have particular requirements not fulfilled by more generalized air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

One known RPT device used for treating sleep disordered breathing is the S9 Sleep Therapy System, manufactured by ResMed, which proves CPAP therapy. Another example of an RPT device is a ventilator. Ventilators such as the ResMed Stellar™ Series of Adult and Paediatric Ventilators may provide invasive and non-invasive non-dependent ventilation therapy for a range of patients for treating a number of conditions such as but not limited to NMD, OHS and COPD.

RPT devices typically comprise a pressure generator, such as a motor-driven blower or a compressed gas reservoir, and are configured to supply pressurized air to the airways of a patient. The outlet of the RPT device is connected via an air circuit to a patient interface such as those described above.

6 BRIEF SUMMARY OF THE TECHNOLOGY

The present technology is directed towards providing medical apparatus used in the diagnosis, amelioration, treatment, or prevention of respiratory disorders having one or more of improved comfort, cost, efficacy, ease of use and manufacturability.

One aspect of the present technology comprises an adaptive servo-ventilator that allows a patient's respiration to be supported in the absence of significant spontaneous respiratory effort in a manner that adapts to the patient's recent spontaneous efforts. In one implementation, the adaptive servo-ventilator delivers backup breaths at a sustained timed backup rate that is a function of the patient's spontaneous respiratory rate.

Another aspect of the present technology comprises an adaptive servo-ventilator that gradually increases the vigilance of the timing threshold for delivering backup breaths from less vigilant to more vigilant. In one implementation, the adaptive servo-ventilator delivers backup breaths at a rate that gradually increases from a spontaneous backup rate to a sustained timed backup rate.

Another aspect of the present technology comprises a CPAP therapy device that is configured to treat Cheyne-Stokes respiration by manipulating the Functional Residual Capacity (FRC) of the patient's lungs. In one implementation, the CPAP device computes the treatment pressure so as to bring a measure indicative of ventilation of the patient towards a target ventilation that is dependent on the measure indicative of ventilation.

Another aspect of the present technology comprises a CPAP therapy device that is configured to treat Cheyne-Stokes respiration by periodically inducing a central apnea in the patient, thereby causing the patient's average $CO_2$ level to rise. In one implementation, the CPAP device elevates the treatment pressure to a high level for a short time, the high level being high enough and the short time being long enough to inflate the lungs and thereby induce a central apnea.

Another aspect of the present technology comprises a servo-ventilator that is configured to treat Cheyne-Stokes respiration by "anti-ventilating" the patient when a measure indicative of ventilation is greater than a threshold. In one implementation, the servo-ventilator oscillates the treatment pressure in antiphase with the patient's spontaneous respiratory efforts when the measure indicative of ventilation is greater than the threshold.

Of course, portions of the aspects may form sub-aspects of the present technology. Also, various ones of the sub-aspects and/or aspects may be combined in various manners and also constitute additional aspects or sub-aspects of the present technology.

The present technology may be implemented in one aspect as an apparatus. The apparatus is preferably directed to treating a respiratory disorder in a patient and comprises a pressure generator configured to generate a supply of air at a positive pressure to an airway of the patient, a sensor configured to generate data representing a property of the supply of air and a controller. The controller is preferably configured to control the pressure generator to generate the supply of air at a positive treatment pressure that oscillates in synchrony with the patient's spontaneous respiratory efforts, wherein the amplitude of the oscillation is the pressure support, compute a measure indicative of ventilation of the patient from the sensor data and control the pressure generator to deliver backup breaths at a backup rate in the absence of significant spontaneous respiratory efforts from the patient, wherein the backup rate increases from a spontaneous backup rate to a sustained timed backup rate.

The apparatus may also be configured to operate so that the spontaneous backup rate is a fraction of the sustained timed backup rate. Further, the controller may be further configured to estimate the spontaneous respiratory rate of the patient, and set the sustained timed backup rate dependent on the estimated spontaneous respiratory rate. Other features of the apparatus may comprise configuring the apparatus so that the increase of the backup rate is according to a predetermined profile such that the backup rate reaches the sustained timed backup rate after a predetermined interval. In addition, the predetermined profile may be a continuous linear profile, the predetermined interval may be a function of the adequacy of current ventilation and/or estimating comprises computing the reciprocal of a measure of central tendency of breath duration over one or more periods when the patient is breathing spontaneously.

Still further, the apparatus may be configured such that the measure of central tendency is one of a mean, a median and/or a trimmed mean. Estimating may also comprise performing interval filtering before computing the measure of central tendency, excluding breaths that are not part of a sequence of predetermined length of spontaneous breaths from the measure of central tendency and/or excluding early and late breaths of a sequence of spontaneous breaths from the measure of central tendency.

Other aspects may include configuring the controller such that it computes target ventilation as a high proportion of, but less than, a typical recent value of the measure indicative of ventilation. In addition, computing the pressure support may use a control strategy drawn from the group consisting of: proportional control, proportional-integral control, proportional-differential control, and proportional-integral-differential control. Alternatively, the pressure support may be computed using discrete control.

In other aspects, the measure indicative of ventilation may comprise an estimate of gross alveolar ventilation, be broadly proportional to the actual ventilation of the patient, or be a peak respiratory flow rate over the inspiratory portion of the breathing cycle. Further still, the measure indicative ventilation may be oxygen saturation.

In another aspect various of the foregoing features of the apparatus may be implemented as a method or process that forms instructions executable via a computer, controller or processor. The executable instructions may be stored or encoded in a computer readable medium or memory and cause the controller, computer or processor to perform the algorithm or method.

In one aspect, the method may involve steps that are useful for treating a respiratory disorder. The method preferably comprises controlling a pressure generator to generate a supply of air at a positive treatment pressure to an airway of the patient, wherein the treatment pressure oscillates in synchrony with the patient's spontaneous respiratory efforts, wherein the amplitude of the oscillation is the pressure support; computing a measure indicative of ventilation of the patient from data representing a property of the supply of air; computing the pressure support so as to bring the measure indicative of ventilation towards a target ventilation that is dependent on the measure indicative of ventilation; and controlling the pressure generator to deliver backup breaths at a backup rate in the absence of significant spontaneous respiratory efforts from the patient, wherein the backup rate increases from a spontaneous backup rate to a sustained timed backup rate.

In yet another aspect, the technology may be implemented as an adaptive servo-ventilator that is configured to implement spontaneous/timed mode using a variable backup rate that increases from a spontaneous backup rate to a sustained timed backup rate. In the servo-ventilator, the spontaneous backup rate may be a fraction of the sustained timed backup rate. In addition, the sustained timed backup rate may be equal to the spontaneous respiratory rate Other apparatus may include those suitable for treating a respiratory disorder in a patient. The apparatus preferably comprises a pressure generator configured to generate a supply of air at a positive pressure to an airway of the patient; a sensor configured to generate data representing a property of the supply of air; and a controller configured to: compute a measure indicative of ventilation of the patient from the sensor data; compute the pressure support so as to bring the measure indicative of ventilation towards a target ventilation that is dependent on the measure indicative of ventilation; estimate the spontaneous respiratory rate of the patient; and control the pressure generator to deliver backup breaths at a sustained timed backup rate in the absence of significant spontaneous respiratory efforts from the patient, wherein the sustained timed backup rate is a function of the estimated spontaneous respiratory rate.

Yet still another aspect an apparatus is provided. The apparatus includes controller configured to compute treatment pressure so as to bring the measure indicative of ventilation towards a target ventilation that is dependent on the measure indicative of ventilation. This apparatus may further include a pressure generator configured to generate a supply of air at a positive pressure to an airway of the patient; a sensor configured to generate data representing a property of the supply of air; and a controller configured to: control the pressure generator to generate the supply of air at a positive treatment pressure that is approximately constant throughout the breathing cycle of the patient; compute a measure indicative of ventilation of the patient from the sensor data; and compute the treatment pressure so as to bring the measure indicative of ventilation towards a target ventilation that is dependent on the measure indicative of ventilation.

In a further aspect, a method is provided for treating a respiratory disorder in a patient, the method comprising: controlling a pressure generator to generate a supply of air at a positive treatment pressure to an airway of the patient, wherein the treatment pressure oscillates in synchrony with the patient's spontaneous respiratory efforts, wherein the amplitude of the oscillation is the pressure support; computing a measure indicative of ventilation of the patient from data representing a property of the supply of air; computing the pressure support so as to bring the measure indicative of ventilation towards a target ventilation that is dependent on the measure indicative of ventilation; estimating the spontaneous respiratory rate of the patient; and controlling the pressure generator to deliver backup breaths at a sustained timed backup rate in the absence of significant spontaneous respiratory efforts from the patient, wherein the sustained timed backup rate is a function of the estimated spontaneous respiratory rate.

A further aspect includes an apparatus with a pressure generator, sensor and controller. The pressure generator is configured to generate a supply of air at a positive pressure to an airway of the patient and the sensor is configured to generate data representing a property of the supply of air. The controller is configured to control the pressure generator to generate the supply of air at a positive treatment pressure that is approximately constant throughout the breathing cycle of the patient; compute a measure indicative of ventilation of the patient from the sensor data; and compute the treatment pressure so as to bring the measure indicative of ventilation towards a target ventilation that is dependent on the measure indicative of ventilation.

An aspect of the technology may also be implemented as a method or process for treating respiratory disorders. The method or process may comprise controlling a pressure generator to generate a supply of air at a positive treatment pressure to an airway of the patient, wherein the treatment pressure oscillates in synchrony with the patient's spontaneous respiratory efforts, wherein the amplitude of the oscillation is the pressure support; computing a measure indicative of ventilation of the patient from data representing a property of the supply of air; and computing the treatment pressure so as to bring the measure indicative of ventilation towards a target ventilation that is dependent on the measure indicative of ventilation.

In yet still a further aspect, an apparatus is provided that comprises a pressure generator configured to generate a supply of air at a positive pressure to an airway of the patient; a sensor configured to generate data representing a property of the supply of air; and a controller configured to: control the pressure generator to generate the supply of air at a positive treatment pressure that is approximately constant throughout the breathing cycle of the patient; and control the pressure generator to periodically elevate the treatment pressure to a high level for a short time, the high level being high enough and the short time being long enough to induce a central apnea in the patient.

Other aspects may include an apparatus for treating a respiratory disorder in a patient, the apparatus comprising: a pressure generator configured to generate a supply of air at a positive pressure to an airway of the patient; a sensor configured to generate data representing a property of the supply of air; and a controller configured to: compute a measure indicative of ventilation of the patient from the sensor data; and control the pressure generator to generate the supply of air at a positive treatment pressure that oscillates in synchrony with the patient's spontaneous respiratory efforts, wherein the amplitude of the oscillation is the pressure support; wherein the treatment pressure oscillates in phase with the patient's spontaneous respiratory efforts when the measure indicative of ventilation is less than a first threshold; and the treatment pressure oscillates in antiphase with the patient's spontaneous respiratory efforts when the measure indicative of ventilation is greater than a second threshold.

Another aspect includes implementation of a method or process for treating respiratory disorders comprising: controlling a pressure generator to generate a supply of air at a positive treatment pressure to an airway of the patient, wherein the treatment pressure oscillates in synchrony with the patient's spontaneous respiratory efforts; and computing a measure indicative of ventilation of the patient from data representing a property of the supply of air; wherein the treatment pressure oscillates in phase with the patient's spontaneous respiratory efforts when the measure of indicative ventilation is less than a first threshold; and the oscillation is in antiphase with the patient's spontaneous respiratory efforts when the measure indicative of ventilation is greater than a second threshold.

Still further aspects of the invention include methods or algorithms that are implemented and stored in memory as instructions that are run on one or more processors.

Other features and aspects of the technology will be apparent from consideration of the information contained in the following detailed description, abstract, drawings and claims.

7 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

7.1 Treatment Systems

FIG. 1A shows a system in accordance with the present technology. A patient 1000 wearing a patient interface 3000 receives a supply of pressurized air from an RPT device 4000. Air from the RPT device 4000 is humidified in a humidifier 5000, and passes along an air circuit 4170 to the patient 1000. A bed partner 1100 is also shown.

7.2 RESPIRATORY SYSTEM AND FACIAL ANATOMY

Figure 1A:
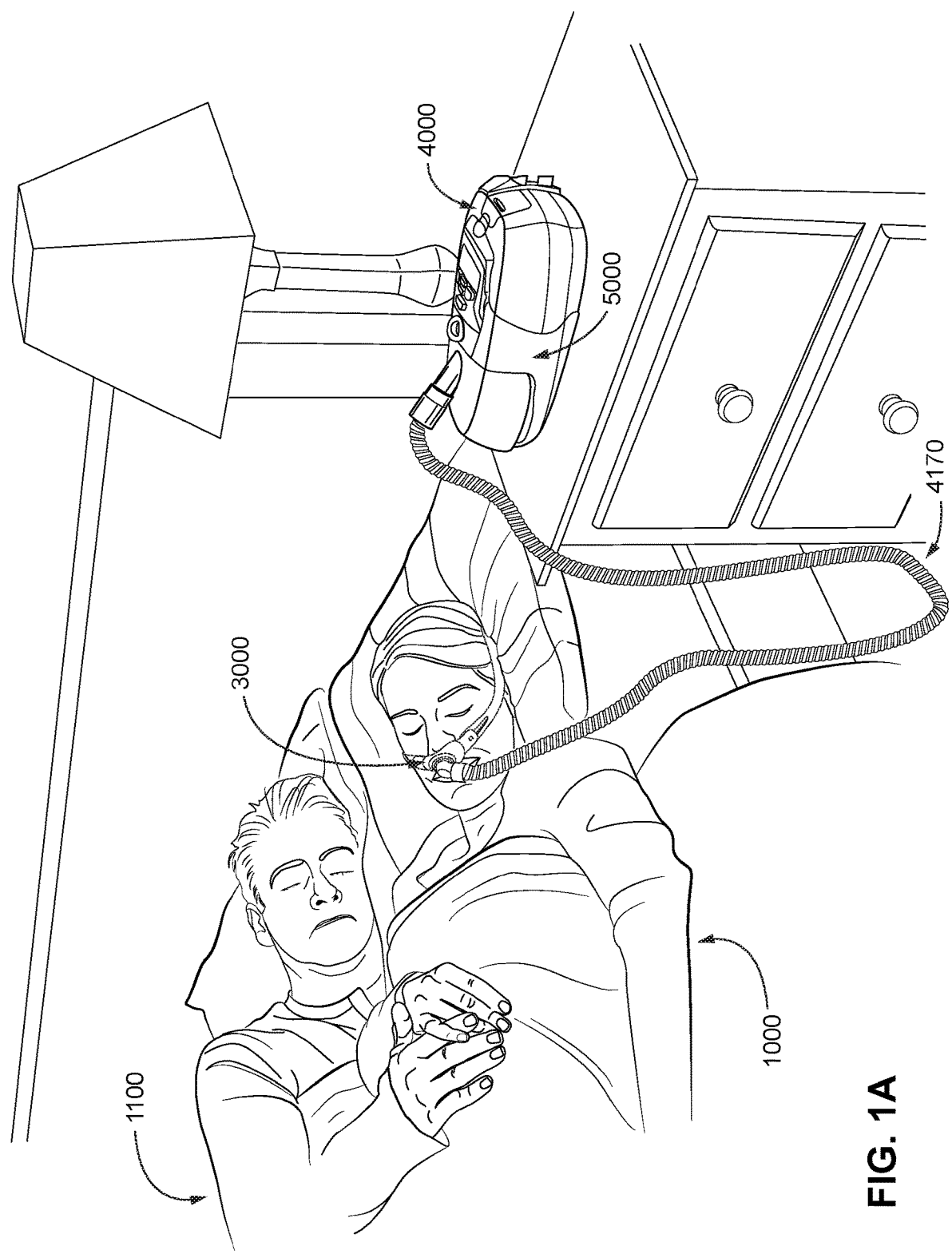
FIG. 1B shows an RPT device 4000 in use on a patient 1000 with a nasal mask 3000.
FIG. 1C shows an RPT device 4000 in use on a patient 1000 with a full-face mask 3000.
Figure 1B:
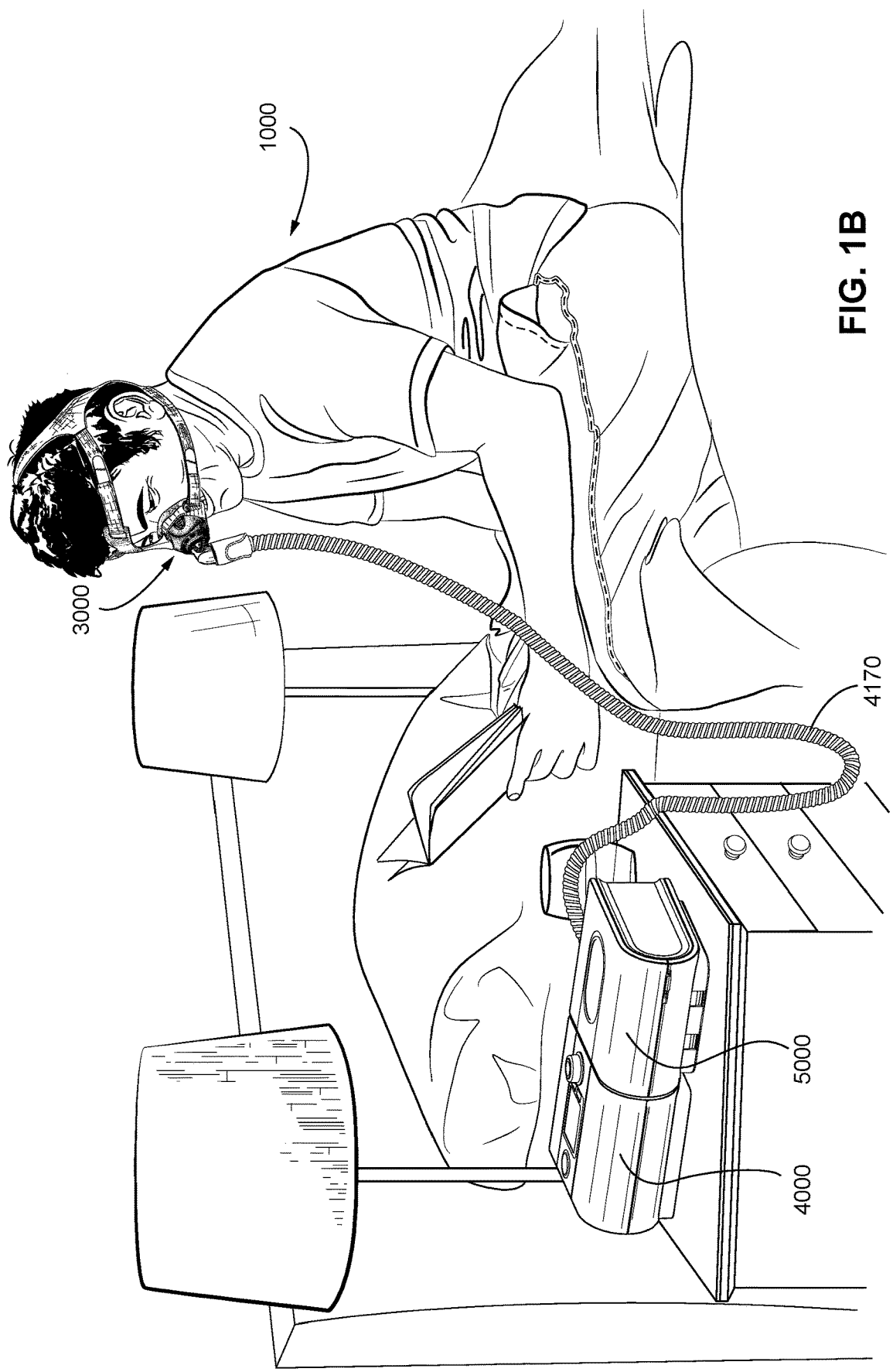
Figure 1C:
Figure 2A:
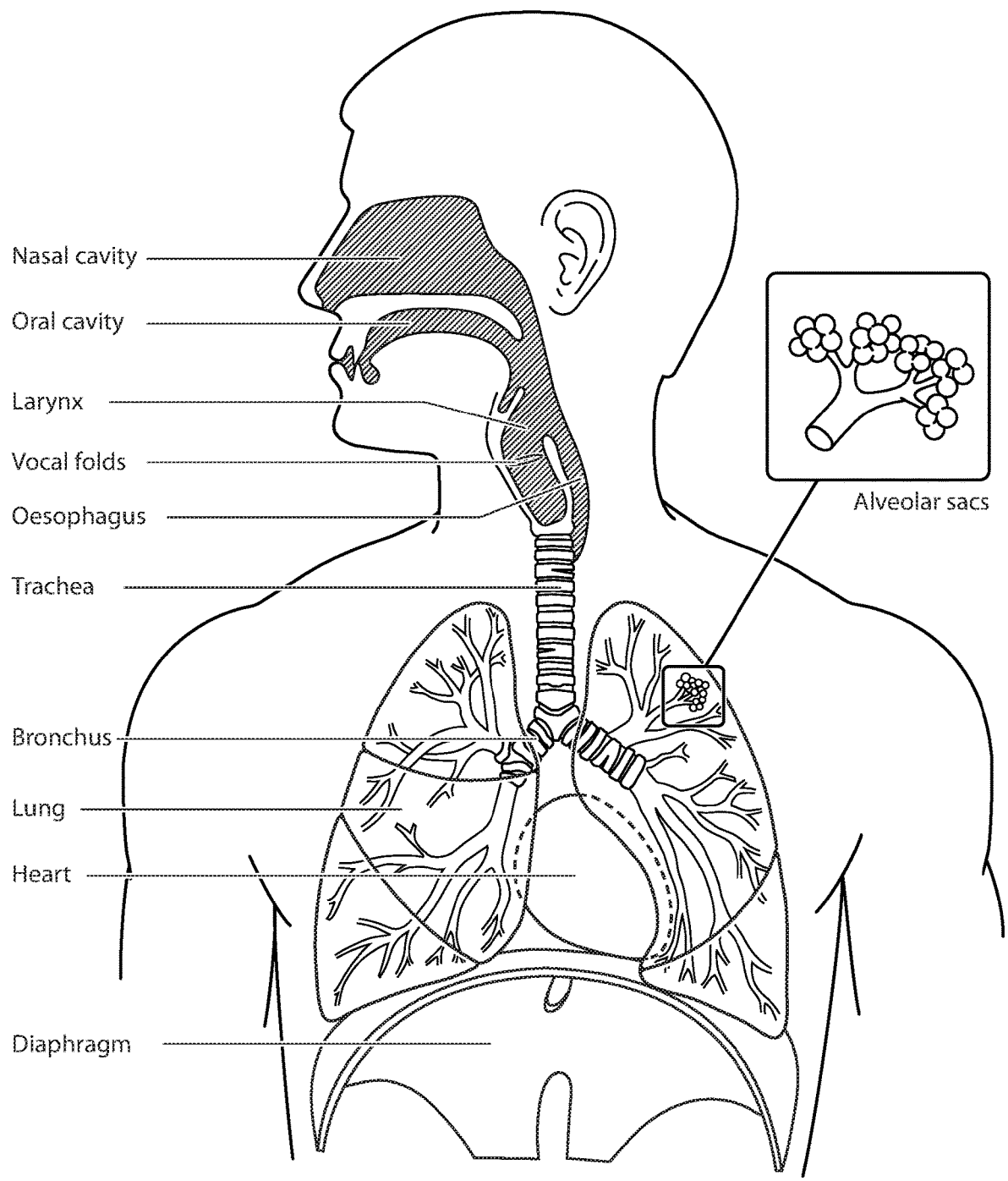

FIG. 2A shows an overview of a human respiratory system including the nasal and oral cavities, the larynx, vocal folds, oesophagus, trachea, bronchus, lung, alveolar sacs, heart and diaphragm.

Figure 2B:
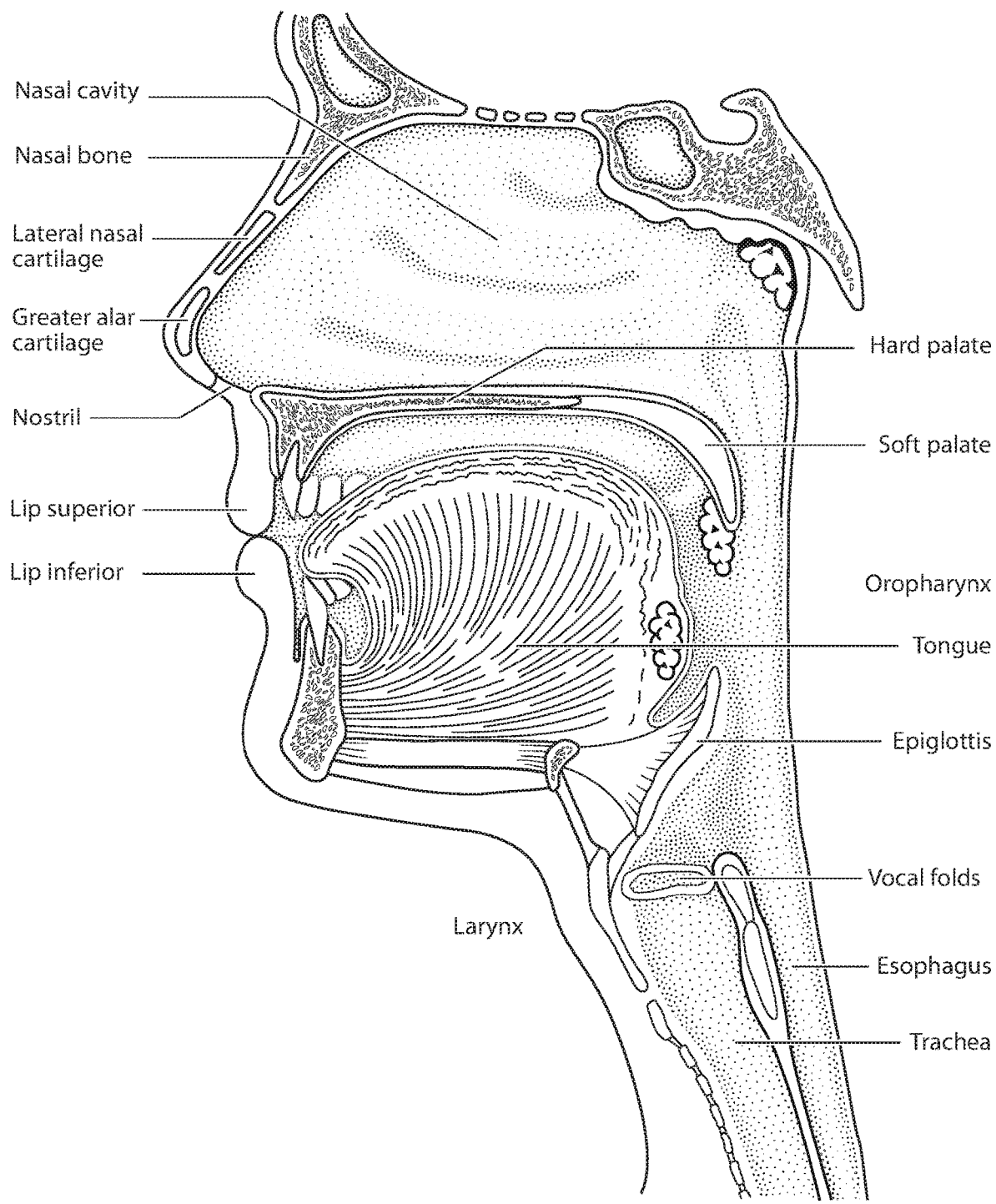

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

7.3 Patient Interface

Figure 3:
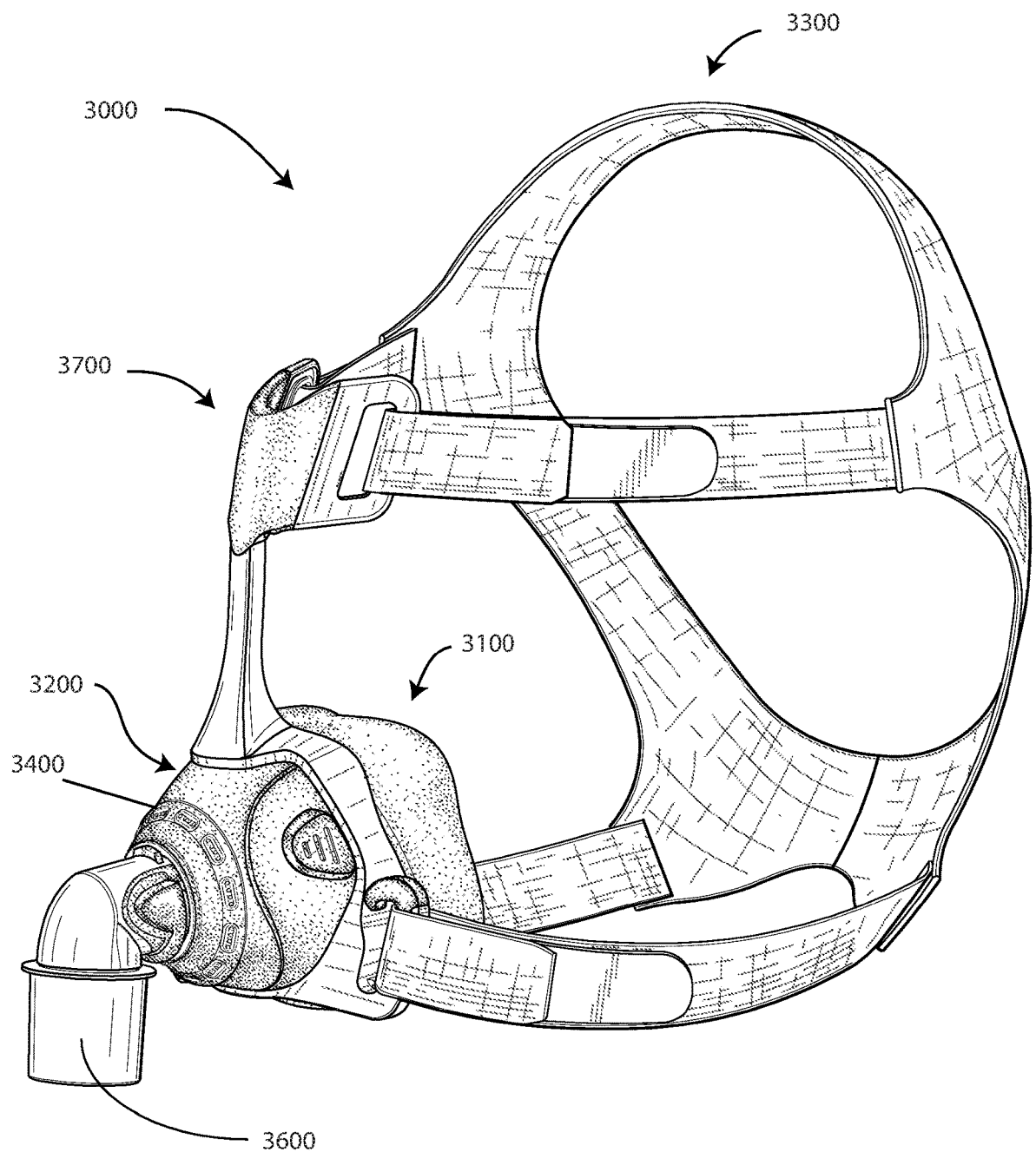

FIG. 3 shows a non-invasive patient interface 3000 in the form of a nasal mask.

7.4 RPT Device

Figure 4A:
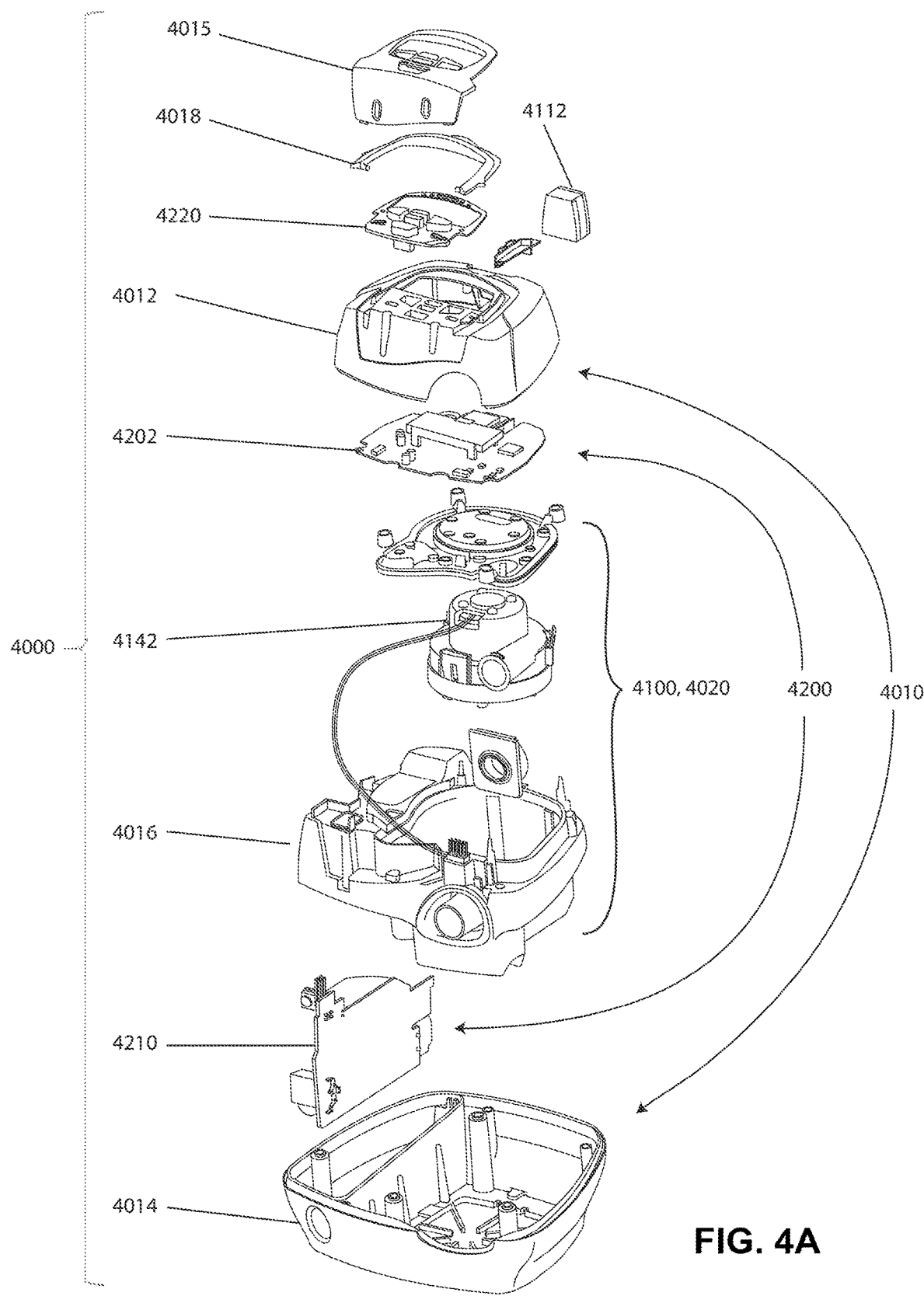

FIG. 4A shows an RPT device 4000 in accordance with one form of the present technology.

Figure 4B:
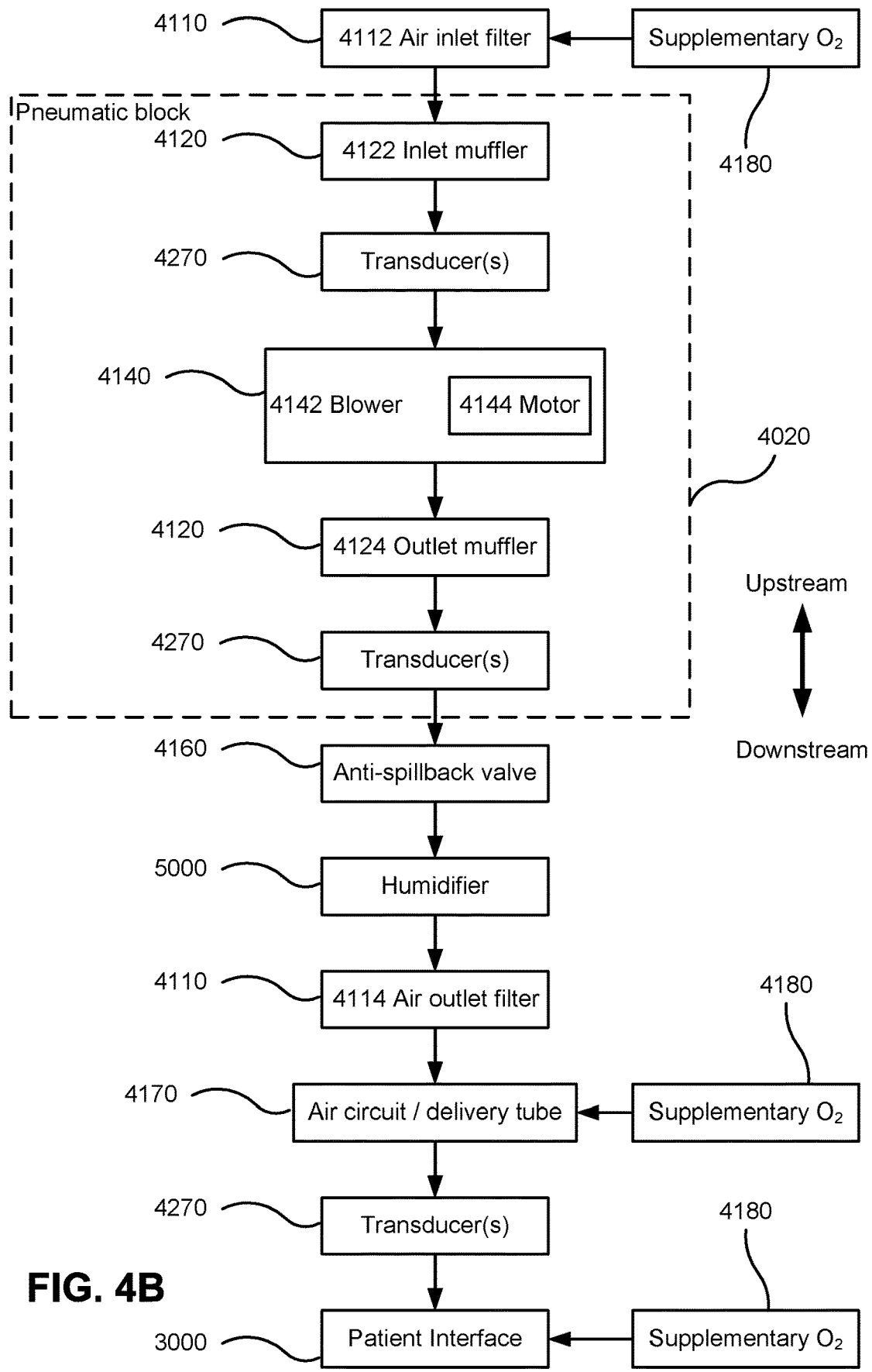

FIG. 4B shows a schematic diagram of the pneumatic circuit of an RPT device 4000 in accordance with one form of the present technology. The directions of upstream and downstream are indicated.

Figure 4C:
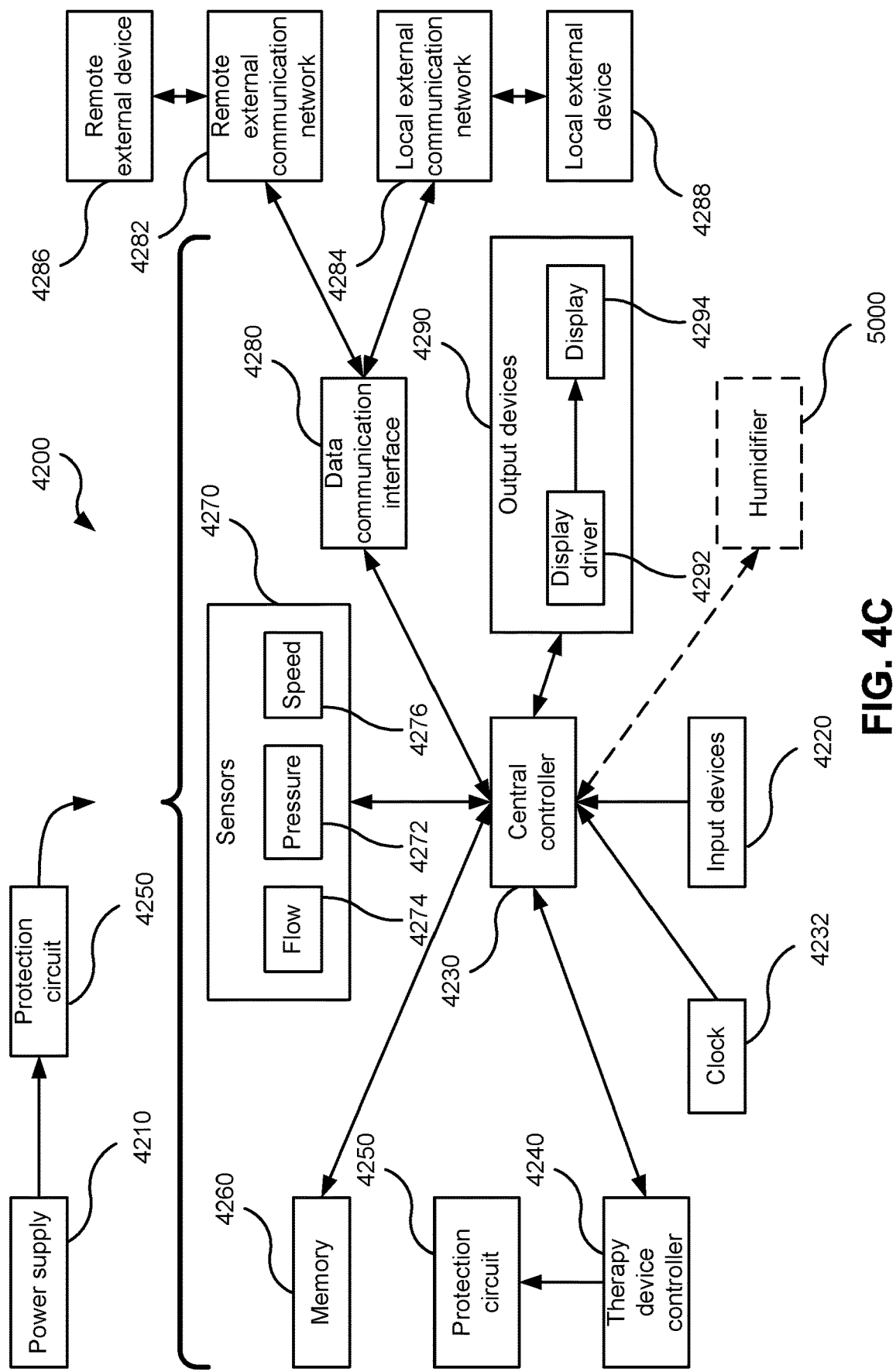

FIG. 4C shows a schematic diagram of the electrical components of an RPT device 4000 in accordance with one aspect of the present technology.

Figure 4D:
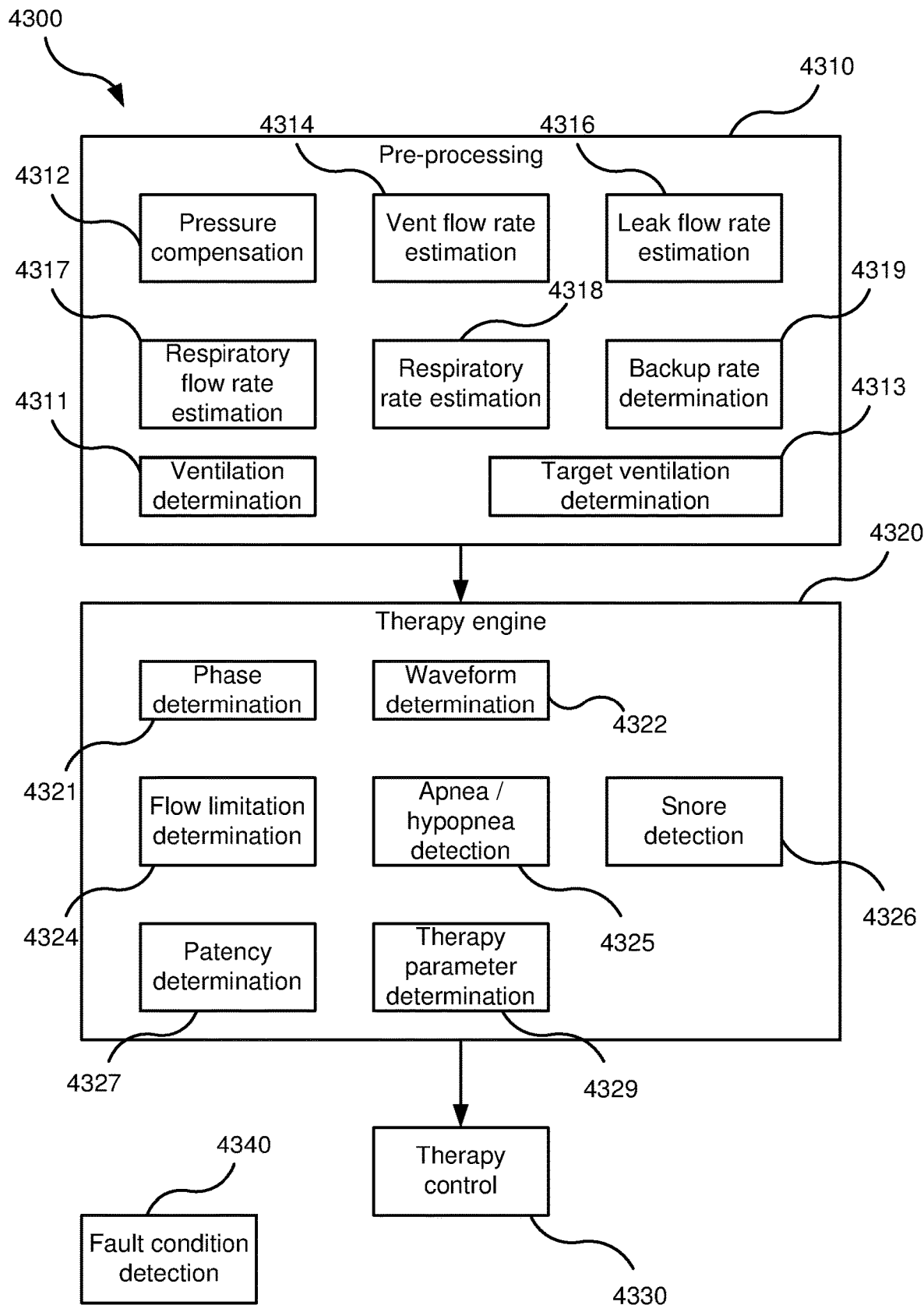

FIG. 4D shows a schematic diagram of the algorithms 4300 implemented in an RPT device 4000 in accordance with an aspect of the present technology. In FIG. 4D, arrows with solid lines indicate an actual flow of information, for example via an electronic signal.

Figure 4E:
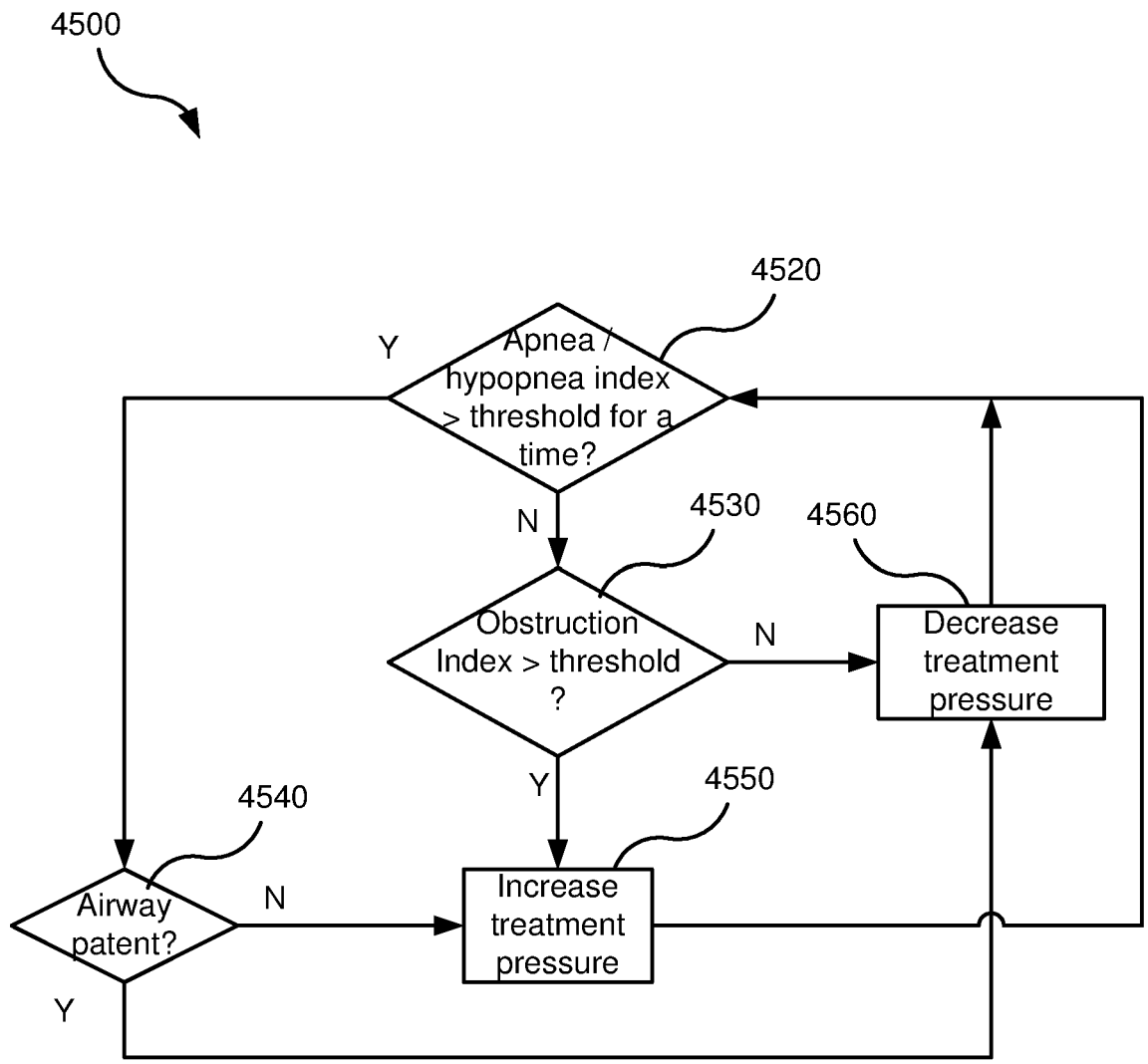

FIG. 4E is a flow chart illustrating a method 4500 carried out by the therapy engine module 4320 of FIG. 4D in accordance with one aspect of the present technology.

7.5 Humidifier

Figure 5:
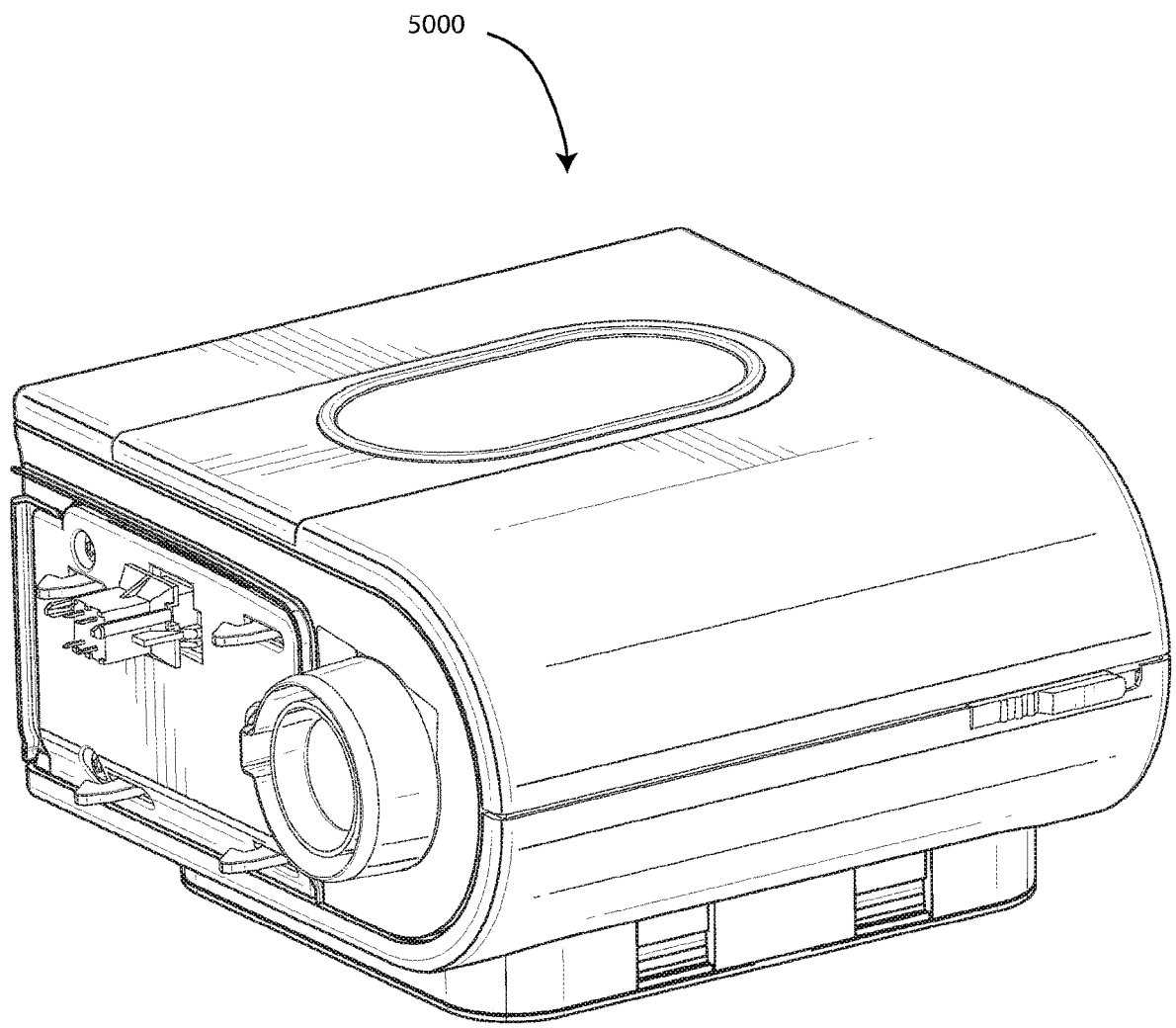

FIG. 5 shows a humidifier 5000.

7.6 Breathing Waveforms

Figure 6A:
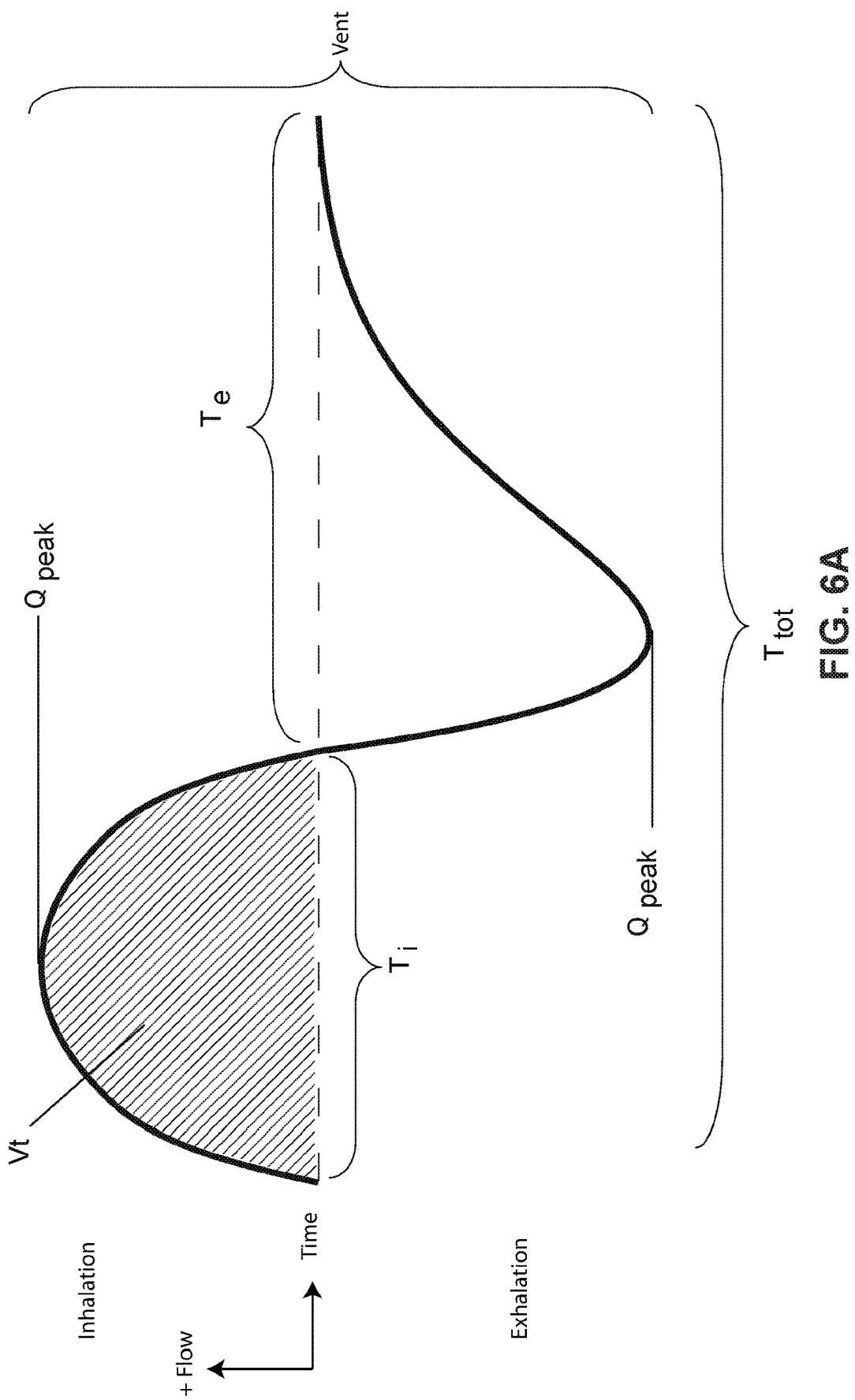

FIG. 6A shows a model typical breath waveform of a person while sleeping.

Figure 6B:
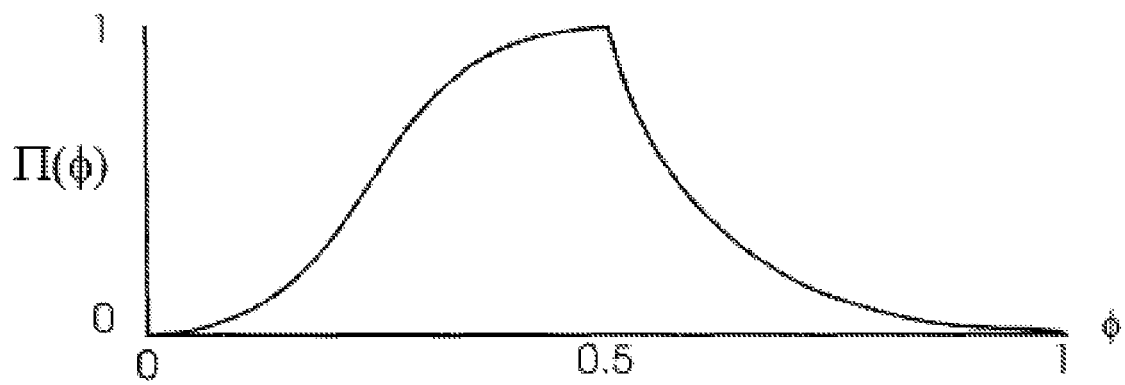

FIG. 6B shows an example of a "shark fin" pressure waveform template.

Figure 6C:
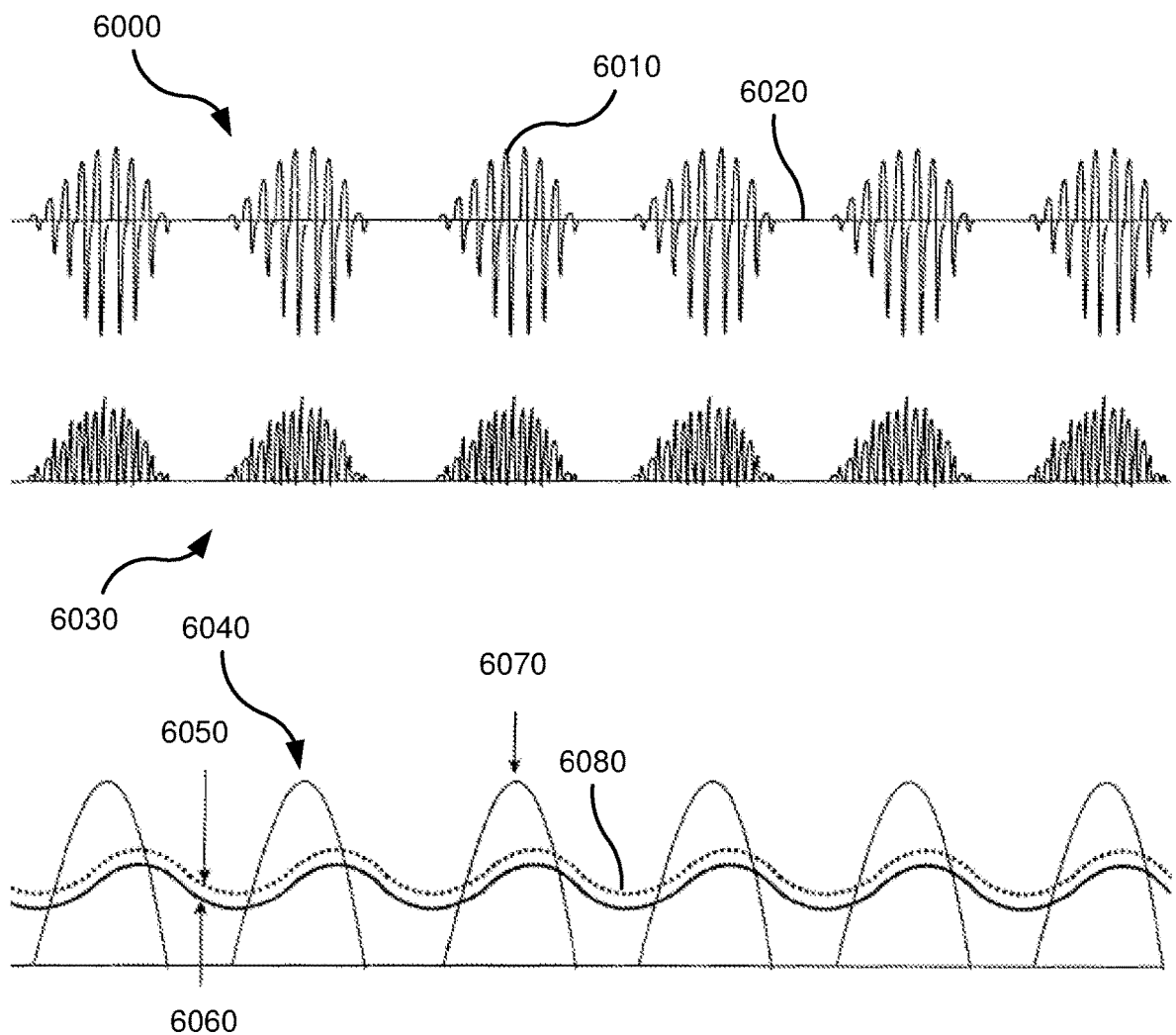

FIG. 6C shows an example of respiratory airflow during Cheyne-Stokes respiration, and various quantities calculated therefrom.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

8.1 Therapy

In one form, the present technology comprises a method for treating a respiratory disorder comprising the step of supplying pressurized air to the airways of a patient 1000.

8.2 Treatment Systems

In one form, the present technology comprises an apparatus or device for treating a respiratory disorder. The apparatus or device may comprise an RPT device 4000 for supplying pressurized air to the patient 1000 via an air circuit 4170 leading to a patient interface 3000.

8.3 Patient Interface

A non-invasive patient interface 3000 in accordance with one aspect of the present technology comprises the following functional aspects: a seal-forming structure 3100, a plenum chamber 3200, a positioning and stabilizing structure 3300, a vent 3400, a connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to an airway of the patient so as to facilitate the supply of pressurized air to the airway.

8.4 RPT Device

FIG. 4A shows an RPT device 4000 in accordance with one aspect of the present technology. The RPT device 4000 comprises mechanical and pneumatic components 4100, electrical components 4200 and is programmed to execute one or more algorithms 4300. The RPT device 4000 may have an external housing 4010 formed in two parts, an upper portion 4012 and a lower portion 4014. The RPT device 4000 may comprise a chassis 4016 that supports one or more internal components of the RPT device 4000. The RPT device 4000 may include at least one panel 4015 and a handle 4018.

As shown in FIGS. 4A-4C, the pneumatic path of the RPT device 4000 may comprise one or more air path items, e.g., an inlet air filter 4112, an inlet muffler 4122, a pressure generator 4140 capable of supplying pressurized air (e.g. a blower 4142), an outlet muffler 4124, and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

8.4.1 RPT Device Mechanical & Pneumatic Components

An RPT device 4000 may comprise one or more of the following components in an integral unit. In an alternative form, one or more of the following components may be located as respective separate units.

8.4.1.1 Air Filter(s)

An RPT device 4000 in accordance with one form of the present technology may include an air filter 4110, or a plurality of air filters 4110.

In one form, an air inlet filter 4112 is located at the beginning of the pneumatic path upstream of a pressure generator 4140.

In one form, an air outlet filter 4114, for example an antibacterial filter, is located between an outlet of the pneumatic block 4020 and a patient interface 3000.

8.4.1.2 Muffler(s)

An RPT device 4000 in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

8.4.1.3 Pressure Generator

In one form of the present technology, a pressure generator 4140 for supplying pressurized air is a controllable blower 4142. For example, the blower 4142 may include a brushless DC motor 4144 with one or more impellers housed in a volute. The pressure generator 4140 may be capable of generating a supply or flow of air, for example at about 120 litres/minute, at a positive pressure in a range from about 4 cmH$_2$O to about 20 cmH$_2$O, or in other forms up to about 30 cmH$_2$O.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

8.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 are constructed and arranged to generate data representing respective properties of the air flow, such as a flow rate, a pressure or a temperature, at that point in the pneumatic path.

In one form of the present technology, one or more transducers 4270 are located proximate to the patient interface 3000.

In one form, a signal from a transducer 4270 may be filtered, such as by low-pass, high-pass or band-pass filtering.

8.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit

An air circuit 4170 in accordance with one aspect of the present technology is a conduit or tube constructed and arranged to allow, in use, a flow of air to travel between two components such as the pneumatic block 4020 and the patient interface 3000.

8.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

8.4.2 RPT Device Electrical Components

8.4.2.1 Power Supply

In one form of the present technology power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

8.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

8.4.2.3 Central Controller

In one form of the present technology, the central controller 4230 is a processor suitable to control an RPT device 4000 such as an x86 INTEL processor.

A central controller 4230 suitable to control an RPT device 4000 in accordance with another form of the present technology includes a processor based on ARM Cortex-M processor from ARM Holdings. For example, an STM32 series microcontroller from ST MICROELECTRONICS may be used.

Another central controller 4230 suitable to control an RPT device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the central controller 4230 for the RPT device 4000. For example a processor from the MSP430 family of microcontrollers, manufactured by TEXAS INSTRUMENTS, may be used.

In another form of the present technology, the central controller 4230 is a dedicated electronic circuit. In another form, the central controller 4230 is an application-specific integrated circuit (ASIC). In another form, the central controller 4230 comprises discrete electronic components.

The central controller 4230 is configured to receive input signal(s) from one or more transducers 4270, one or more input devices 4220, and the humidifier 5000.

The central controller 4230 is configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein such as the one or more algorithms 4300 expressed as computer programs stored in a non-transitory computer readable storage medium, such as memory 4260. In some forms of the present technology, as previously discussed, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

While the central controller 4230 may comprise a single controller interacting with various sensors 4270, data communications interface 4280, memory 4260, as well as other devices, the functions of controller 4230 may be distributed among more than one controller. Thus, the term "central" as used herein is not meant to limit the architecture to a single controller or processor that controls the other devices. For example, alternative architectures may include a distributed controller architecture involving more than one controller or processor. This may include, for example, a separate local (i.e., within RPT device 4000) or remotely located controller that perform some of the algorithms 4300, or even more than one local or remote memory that stores some of the algorithms. In addition, the algorithms when expressed as computer programs may comprise high level human readable code (e.g., C++, Visual Basic, other object oriented languages, etc.) or low/machine level instructions (Assembler, Verilog, etc.). Depending on the functionality of an algorithm(s), such code or instructions may be burnt in the controller, e.g., an ASIC or DSP, or be a run time executable ported to a DSP or general purpose processor that then becomes specifically programmed to perform the tasks required by the algorithm(s).

8.4.2.4 Clock

The RPT device 4000 may include a clock 4232 that is connected to the central controller 4230.

8.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

8.4.2.6 Protection Circuits

An RPT device 4000 in accordance with the present technology may comprise one or more protection circuits 4250.

One form of protection circuit 4250 in accordance with the present technology is an electrical protection circuit.

One form of protection circuit 4250 in accordance with the present technology is a temperature or pressure safety circuit.

8.4.2.7 Memory

In accordance with one form of the present technology the RPT device 4000 includes memory 4260, for example non-volatile memory. In some forms, memory 4260 may include battery powered static RAM. In some forms, memory 4260 may include volatile RAM.

Memory 4260 may be located on PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

8.4.2.8 Transducers

Transducers may be internal of the device 4000, or external of the RPT device 4000. External transducers may be located for example on or form part of the air delivery circuit 4170, e.g. at the patient interface 3000. External transducers may be in the form of non-contact sensors such as a Doppler radar movement sensor that transmit or transfer data to the RPT device 4000.

8.4.2.8.1 Flow Rate

A flow rate transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In one example, a signal representing total flow rate Qt from the flow transducer 4274 is received by the central controller 4230.

8.4.2.8.2 Pressure

A pressure transducer 4272 in accordance with the present technology is located in fluid communication with the pneumatic path. An example of a suitable pressure transducer 4272 is a sensor from the HONEYWELL ASDX series. An alternative suitable pressure transducer is a sensor from the NPA Series from GENERAL ELECTRIC.

In use, a signal from the pressure transducer 4272 is received by the central controller 4230. In one form, the signal from the pressure transducer 4272 is filtered prior to being received by the central controller 4230.

8.4.2.8.3 Motor Speed

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

8.4.2.9 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilizes one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorized person such as a clinician.

The local external device 4288 may be a personal computer, mobile phone, tablet or remote control.

8.4.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

8.4.2.10.1 Display Driver

A display driver 4292 receives as an input the characters, symbols, or images intended for display on the display 4294, and converts them to commands that cause the display 4294 to display those characters, symbols, or images.

8.4.2.10.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.3 RPT Device Algorithms

8.4.3.1 Pre-Processing Module

A pre-processing module 4310 in accordance with the present technology receives, as an input, raw data from a transducer 4270, for example a flow rate sensor 4274 or a pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, respiratory flow rate estimation 4317, ventilation determination 4311, target ventilation determination 4313, respiratory rate estimation 4318, and backup rate determination 4319.

8.4.3.1.1 Pressure Compensation

In one form of the present technology, a pressure compensation algorithm 4312 receives as an input a signal indicative of the pressure in the pneumatic path proximal to an outlet of the pneumatic block 4020. The pressure compensation algorithm 4312 estimates the pressure drop in the air circuit 4170 and provides as an output an estimated pressure, Pm, in the patient interface 3000.

8.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

8.4.3.1.3 Leak Flow Rate Estimation

In one form of the present technology, a leak flow rate estimation algorithm 4316 receives as an input a total flow rate Qt and a vent flow rate Qv, and estimates a leak flow rate Ql. In one form, the leak flow rate estimation algorithm 4316 estimates the leak flow rate Ql by calculating an average of the difference between the total flow rate and the vent flow rate Qv over a period sufficiently long to include several breathing cycles, e.g. about 10 seconds.

In one form, the leak flow estimation algorithm 4316 receives as an input a total flow rate Qt, a vent flow rate Qv, and an estimated pressure, Pm, in the patient interface 3000, and estimates a leak flow rate Ql by calculating a leak conductance, and determining a leak flow rate Ql to be a function of leak conductance and the pressure Pm. Leak conductance may be calculated as the quotient of low-pass filtered non-vent flow rate equal to the difference between total flow rate Qt and vent flow rate Qv, and low-pass filtered square root of pressure Pm, where the low-pass filter time constant has a value sufficiently long to include several breathing cycles, e.g. about 10 seconds. The leak flow rate Ql may be estimated as the product of leak conductance and a function of pressure, Pm.

8.4.3.1.4 Respiratory Flow Rate Estimation

In one form of the present technology, a respiratory flow rate estimation algorithm 4317 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

In other forms of the present technology, the respiratory flow estimation algorithm 4317 provides a value that acts as a proxy for the respiratory flow rate Qr. Possible proxies for respiratory flow rate include:
  Respiratory movement of the chest of the patient 1000
  Current drawn by the pressure generator 4140
  Motor speed of the pressure generator 4140
  Trans-thoracic impedance of the patient 1000
The respiratory flow rate proxy value may be provided by a transducer 4270 in the RPT device 4000, e.g. the motor speed sensor 4276, or a sensor external to the RPT device 4000, such a respiratory movement sensor or a trans-thoracic impedance sensor.

8.4.3.1.5 Ventilation Determination

In one form of the present technology, a ventilation determination algorithm 4311 receives an input a respiratory flow rate Qr, and determines a measure Vent indicative of current patient ventilation.

In some implementations, the ventilation determination algorithm 4311 determines a measure of ventilation Vent that is an estimate of actual patient ventilation.

In one such implementation, the measure of ventilation Vent is half the absolute value of respiratory flow, Qr, optionally filtered by low-pass filter such as a second order Bessel low-pass filter with a corner frequency of 0.11 Hz.

In one such implementation, the measure of ventilation Vent is an estimate of gross alveolar ventilation (i.e. non-anatomical-deadspace ventilation). This requires an estimate of anatomical deadspace. One can use the patient's height (or arm-span in cases of severe skeletal deformity) as a good predictor of anatomical deadspace. Gross alveolar ventilation is then equal to a measure of actual patient ventilation, e.g. determined as above, less the product of the estimated anatomical deadspace and the estimated spontaneous respiratory rate Rs.

In other implementations, the ventilation determination algorithm 4311 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalized in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate waveform shape is constant.

In other forms, the ventilation determination algorithm 4311 determines a measure Vent of ventilation that is not based on respiratory flow rate Qr, but is a proxy for the current patient ventilation, such as oxygen saturation ($SaO_2$), or partial pressure of carbon dioxide ($PCO_2$), obtained from suitable sensors attached to the patient 1000.

8.4.3.1.6 Target Ventilation Determination

In one form of the present technology, a central controller 4230 takes as input the measure of current ventilation, Vent, and executes one or more target ventilation determination algorithms 4313 for the determination of a target value Vtgt for the measure of ventilation.

In some forms of the present technology, there is no target ventilation determination algorithm 4313, and the target ventilation Vtgt is predetermined, for example by hard-coding during configuration of the RPT device 4000 or by manual entry through the input device 4220.

In other forms of the present technology, such as adaptive servo-ventilation (ASV) therapy (described below), the target ventilation determination algorithm 4313 computes the target ventilation Vtgt from a value Vtyp indicative of the typical recent ventilation of the patient 1000.

In some forms of adaptive servo-ventilation therapy, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation therapy, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4313, the recent history is of the order of several minutes, but in any case should be longer than the timescale of Cheyne-Stokes waxing and waning cycles. The target ventilation determination algorithm 4313 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

8.4.3.1.7 Respiratory Rate Estimation

In one form of the present technology, a respiratory rate estimation algorithm 4318 receives as an input a respiratory flow rate, Qr, to the patient 1000, and produces an estimate of the spontaneous respiratory rate Rs of the patient.

The respiratory rate estimation algorithm 4318 may estimate the spontaneous respiratory rate Rs over periods when the patient 1000 is breathing spontaneously, i.e. when the RPT device 4000 is not delivering "backup breaths" (described below). In some forms of the present technology, the respiratory rate estimation algorithm 4318 estimates the respiratory rate over periods when servo-assistance (defined as pressure support minus minimum pressure support) is low, in one implementation less than 4 $cmH_2O$, as such periods are more likely to reflect spontaneous respiratory effort.

In some forms of the present technology, the respiratory rate estimation algorithm 4318 estimates the respiratory rate over periods of asleep breathing, since the respiratory rate during these periods may be substantially different from the respiratory rate during wake. Anxiety typically results in a higher respiratory rate than that prevailing during sleep. When patients focus on their own breathing process, their respiratory rates are typically lower than those during normal wakefulness or during sleep. Techniques such as described in Patent Application no. PCT/AU2010/000894, published as WO 2011/006199, the entire disclosure of which is hereby incorporated herein by reference, may be used to identify periods of awake breathing from the respiratory flow rate, Qr.

In some forms of the present technology, the respiratory rate estimation algorithm 4318 estimates the spontaneous respiratory rate Rs as the reciprocal of one of a variety of well-known statistical measures of central tendency of breath duration Ttot during the period of interest. In such measures it is desirable to reject, or at least be robust to, outliers. One such measure, trimmed mean, in which the lower and upper K proportions of the sorted breath durations are discarded and the mean calculated on the remaining breath durations, is robust to outliers. For example, when K is 0.25, this amounts to discarding the upper and lower quartiles of breath duration Ttot. The median is another robust measure of central tendency, though this can occasionally give unsatisfactory results when the distribution is strongly bimodal. A simple mean may also be employed as a measure of central tendency, though it is sensitive to outliers. An initial interval filtering stage, in which contiguous time intervals corresponding to implausible respiratory rates (e.g. greater than 45 breaths/minute or less than 6 breaths/minute) are excluded as outliers from the mean calculation, may be employed. Other filtering mechanisms which may be used alone or in combination with interval filtering are to exclude any breaths that are not part of a sequence of N successive spontaneous breaths, where N is some small integer (e.g. 3), and to exclude the early and late breaths of a sequence of successive spontaneous breaths, e.g. to exclude the first and last breaths of a sequence of four breaths. The rationale for the latter mechanism is that the first and the last breaths in particular, and the early and late breaths in general, of a sequence of spontaneous breaths may be atypical; for example, the first spontaneous breath may occur as a result of an arousal, and the last spontaneous breath may be longer because of the decreasing respiratory drive which results in the backup breath which ends the sequence of spontaneous breaths.

In some forms of the present technology, the respiratory rate estimation algorithm 4318 makes an initial estimate of the spontaneous respiratory rate Rs using an initial period of estimation, to enable the subsequent processing in the therapy engine module 4320 to begin, and then continuously updates the estimate of the spontaneous respiratory rate Rs using a period of estimation that is longer than the initial period of estimation, to improve statistical robustness. For example, the initial period of estimation may be 20 minutes of suitable spontaneous breaths, but the period of estimation may then progressively increase up to some maximum duration, for example 8 hours. Rather than a rolling window of this duration being used for this estimation, low-pass filters on breath duration may be used, with progressively longer response times (more precisely, progressively lower corner frequencies) as the session proceeds.

In some forms, a suitably processed short-term (e.g. 10-minute) measure of central tendency, such as trimmed mean, may be input to a suitable low-pass filter to give an estimate Rs which changes on the time scale of hours or longer. This has the advantage that potentially large amounts of breath duration data do not need to be stored and processed, as might occur if a trimmed mean needs to be calculated on a moving window of breath duration data lasting hours or days.

In some forms of the present technology, respiratory rates measured over short periods of time, and in particular over one breath, may also be used instead of breath duration in the above-described measures of central tendency, giving generally similar but not identical results.

8.4.3.1.8 Backup Rate Determination

In one form of the present technology, a backup rate determination algorithm 4319 receives as input a spontaneous respiratory rate estimate Rs provided by the respiratory rate estimation algorithm 4318 and returns a "backup rate" Rb. The backup rate Rb is the rate at which the RPT device 4000 will deliver backup breaths, i.e. continue to provide ventilatory support, to a patient 1000 in the absence of significant spontaneous respiratory effort.

In one form of the pre-processing module 4310, there is no backup rate determination algorithm 4319, and the backup rate Rb is instead provided manually to the RPT device 4000, e.g. via the input device 4220, or hard-coded at the time of configuration of the RPT device 4000.

In one form, known as adaptive backup rate, the backup rate determination algorithm 4319 determines the backup rate Rb as a function of the spontaneous respiratory rate Rs. In one implementation, the function determines the backup rate Rb as the spontaneous respiratory rate Rs minus a constant such as 2 breaths per minute. In another implementation, the function determines the backup rate Rb as the spontaneous respiratory rate Rs multiplied by a constant that is slightly less than unity.

In one form, known as variable backup rate, the backup rate determination algorithm 4319 determines the backup rate Rb as a function of time. The backup rate Rb is initialized to a value known as the spontaneous backup rate (SBR) that is some fraction of a final target backup rate, known as the sustained timed backup rate (STBR). The fraction may be two thirds, or three quarters, or other positive values less than one. The SBR is the reciprocal of the timeout period to a backup breath when the most recent inspiration was a spontaneous (i.e. patent-triggered) breath. The STBR may be predetermined (e.g. by manual entry or hard-coding as described above) or set to some typical respiratory rate such as 15 bpm. Over time elapsed since the previous spontaneous breath, the backup rate Rb is increased from the SBR towards the STBR. The increase may be according to a predetermined profile, such as a series of steps, or a continuous linear profile. The profile is chosen such that the backup rate Rb reaches the STBR after a predetermined interval. The interval may be measured in units of time, such as 30 seconds, or relative to the patient's respiration, such as 5 breaths.

In some forms of variable backup rate, the predetermined interval over which the backup rate Rb increases from the SBR towards the STBR may be a function of the adequacy of current ventilation. In one implementation, suitable for servo-ventilation in which a target value Vtgt exists for the measure of ventilation, the backup rate approaches the STBR faster to the extent that current measure of ventilation Vent is less than the target ventilation Vtgt.

In one form of variable backup rate, known as adaptive variable backup rate, the backup rate determination algorithm 4319 determines the backup rate Rb as a function of the current estimated spontaneous respiratory rate Rs provided by the respiratory rate estimation algorithm 4318, as well as a function of time. As in variable backup rate determination, adaptive variable backup rate determination increases the backup rate Rb from the SBR towards the STBR over a predetermined interval that may be a function of the adequacy of current ventilation. The STBR may be initialized to a standard respiratory rate, such as 15 bpm. Once a reliable estimate of spontaneous respiratory rate Rs is available from the respiratory rate estimation algorithm 4318, the STBR may be set to the current estimated spontaneous respiratory rate Rs multiplied by some constant. The SBR may be set to some fraction of the STBR, as in variable backup rate. In one form, the fraction, for example two thirds, can be set to a lower value, such as 0.55, during the initial period of estimation of the spontaneous respiratory rate Rs, to accommodate occasional long breath durations in patients with relatively low respiratory rates, such as 12 breaths per minute.

In some forms, the constant by which the current estimated spontaneous respiratory rate Rs is multiplied to obtain the STBR may be slightly higher than 1, e.g. 1.1, to provide more aggressive ventilation during apneas, which may be desirable in short apneas. The constant may be somewhat lower than 1, e.g. 0.8, particularly if difficulty in resynchronisation with the patient on the return of patient effort turns out to be a problem in a particular patient. Lower backup rates make resynchronisation easier, by lengthening the expiratory pause, during which resynchronisation commonly occurs.

8.4.3.2 Therapy Engine Module

In one form of the present technology, a therapy engine module 4320 receives as inputs one or more of a pressure, Pm, in a patient interface 3000, a respiratory flow rate of air to a patient, Qr, and an estimate Rs of the spontaneous respiratory rate, and provides as an output one or more therapy parameters. In various forms, the therapy engine module 4320 comprises one or more of the following algorithms: phase determination 4321, waveform determination 4322, inspiratory flow limitation determination 4324, apnea/hypopnea determination 4325, snore detection 4326, airway patency determination 4327, and therapy parameter determination 4329.

8.4.3.2.1 Phase Determination

In one form of the present technology, a phase determination algorithm 4321 receives as an input a signal indicative of respiratory flow, Qr, and provides as an output a phase $\Phi$ of a current breathing cycle of a patient 1000.

In some forms, known as discrete phase determination, the phase output $\Phi$ is a discrete variable. One implementation of discrete phase determination provides a bi-valued phase output $\Phi$ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output $\Phi$ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold.

Another implementation of discrete phase determination provides a tri-valued phase output $\Phi$ with a value of one of inhalation, mid-inspiratory pause, and exhalation.

In other forms, known as continuous phase determination, the phase output $\Phi$ is a continuous value, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, a continuous value of phase $\Phi$ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's respiratory rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the inhalation time Ti and the exhalation time Te are first estimated from the respiratory flow rate Qr. The phase $\Phi$ is then determined as the half the proportion of the inhalation time Ti that has elapsed since the previous trigger instant, or 0.5 revolutions plus half the proportion of the exhalation time Te that has elapsed since the previous cycle instant (whichever was more recent).

In some forms of the present technology, suitable for pressure support ventilation therapy (described below), the phase determination algorithm 4321 is configured to trigger even when the respiratory flow rate Qr is insignificant, such as during an apnea. As a result, the RPT device 4000 delivers "backup breaths" in the absence of spontaneous respiratory effort from the patient 1000. For such forms, known as spontaneous/timed (S/T) modes, the phase determination algorithm 4321 may make use of the backup rate Rb provided by the backup rate determination algorithm 4319.

A phase determination algorithm 4321 that uses "fuzzy phase" may implement S/T mode using the backup rate Rb by including a "momentum" rule in the fuzzy phase rules. The effect of the momentum rule is to carry the continuous phase forward from exhalation to inhalation at the backup rate Rb if there are no features of respiratory flow rate Qr that would otherwise carry the continuous phase forward through the other rules. In one implementation, the more it is true that the measure of ventilation Vent (described below) is well below a target value Vtgt for ventilation (also described below), the more highly the momentum rule is weighted in the combination. However, as a result of the rapid increase in pressure support in response to mild to moderate hypoventilation (with respect to the target ventilation), the ventilation may be quite close to the target ventilation. It is desirable that the momentum rule is given a low weighting when the ventilation is close to target, to allow the patient to breathe at rates significantly lower than the respiratory rate at other times (when the patient is not in a central apnea) without being unnecessarily pushed to breathe at a higher rate by the ventilator. However, when the momentum rule is given a low weighting when ventilation is above a value which is below but close to the target ventilation, adequate ventilation may easily be achieved at a relatively high pressure support at a rate well below the backup rate. It would be desirable for the backup breaths to be delivered at a higher rate, because this would enable the target ventilation to be delivered at a lower pressure support. This is desirable for a number of reasons, a key one of which is to diminish mask leak.

To summarize, in a fuzzy phase determination algorithm 4321 that implements S/T mode, there is a dilemma in choosing the weighting for the momentum rule incorporating the backup rate Rb: if it is too high, the patient may feel "pushed along" by the backup rate. If it is too low, the pressure support may be excessive. Hence it is desirable to provide methods of implementing S/T mode which do not rely on the momentum rule described above.

A phase determination algorithm 4321 (either discrete, or continuous without a momentum rule) may implement S/T mode using the backup rate Rb in a manner known as timed backup. Timed backup may be implemented as follows: the phase determination algorithm 4321 attempts to detect the start of inhalation due to spontaneous respiratory effort, for example by monitoring the respiratory flow rate Qr as described above. If the start of inhalation due to spontaneous respiratory effort is not detected within a period of time after the last trigger instant whose duration is equal to the reciprocal of the backup rate Rb (an interval known as the backup timing threshold), the phase determination algorithm 4321 sets the phase output Φ to a value of inhalation (thereby triggering the RPT device 4000). Once the RPT device 4000 is triggered, and a backup breath begins to be delivered, the phase determination algorithm 4321 attempts to detect the start of spontaneous exhalation, for example by monitoring the respiratory flow rate Qr, upon which the phase output Φ is set to a value of exhalation (thereby cycling the RPT device 4000).

If the backup rate Rb is increased over time from the SBR to the STBR, as in a variable backup rate system described above, the backup timing threshold starts out longer and gradually becomes shorter. That is, the RPT device 4000 starts out less vigilant and gradually becomes more vigilant to lack of spontaneous respiratory effort as more backup breaths are delivered. Such an RPT device 4000 is less likely to make a patient feel "pushed along" if they would prefer to breathe at a lower than standard rate, while still delivering backup breaths when they are needed.

If the STBR in a variable backup rate system adapts to the patient's estimated spontaneous respiratory rate Rs, as in an adaptive variable backup rate system described above, the backup breaths will be delivered at a rate that adapts to the patient's own recent spontaneous respiratory efforts.

8.4.3.2.2 Waveform Determination

In one form of the present technology, the therapy control module 4330 controls a pressure generator 4140 to provide a treatment pressure Pt that varies as a function of phase Φ of a breathing cycle of a patient according to a waveform template Π(Φ).

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. One example of such a "smooth and comfortable" waveform template is the "shark fin" waveform template illustrated in FIG. 6B, in which the rise is a raised cosine, and the smooth decay is quasi-exponential (so that the limit of Π as Φ approaches one revolution is precisely zero).

In some forms of the present technology, the waveform determination algorithm 4322 selects a waveform template Π(Φ) from a library of waveform templates, dependent on a setting of the RPT device 4000. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parameterized by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant (transition from exhalation to inhalation). In one such form, the waveform determination algorithm 4322 computes the waveform template Π(Φ,t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π(Φ, t), and Ti is the inhalation time. In one such form, the inspiratory portion $\Pi_i(t)$ of the waveform template is a smooth rise from 0 to 1 parameterized by a rise time, and the expiratory portion $\Pi_e(t)$ of the waveform template is a smooth fall from 1 to 0 parameterized by a fall time.

8.4.3.2.3 Determination of Inspiratory Flow Limitation

In one form of the present technology, a processor executes one or more algorithms 4324 for the detection of inspiratory flow limitation (partial obstruction).

In one form the algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified based on the phase Φ estimated at each instant. For example, the inspiratory portion of the breath is the values of respiratory flow for which the phase Φ is less than or equal to 0.5. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by central controller 4230 for the preceding several inspiratory events. This is repeated over the same inspiratory events for the second such point, and so on. Thus, for example, sixty five scaled data points are generated by central controller 4230, and represent a moving average of the preceding several inspiratory events, e.g. three events. The moving average of continuously updated values of the (e.g. sixty five) points are hereinafter called the "scaled flow", designated as $Q_s(t)$. Alternatively, a single inspiratory event can be utilized rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

8.4.3.2.4 Determination of Apneas and Hypopneas

In one form of the present technology, a central controller 4230 executes one or more algorithms 4325 for the detection of apneas and/or hypopneas.

In one form, the one or more apnea/hypopnea detection algorithms 4325 receive as an input a respiratory flow rate Qr and provide as an output a flag that indicates that an apnea or a hypopnea has been detected.

In one form, an apnea will be said to have been detected when a function of respiratory flow rate Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow rate Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

8.4.3.2.5 Detection of Snore

In one form of the present technology, a central controller 4230 executes one or more snore detection algorithms 4326 for the detection of snore.

In one form, the snore detection algorithm 4326 receives as an input a respiratory flow rate signal Qr and provides as an output a metric of the extent to which snoring is present.

The snore detection algorithm 4326 may comprise a step of determining the intensity of the flow rate signal in the range of 30-300 Hz. The snore detection algorithm 4326 may further comprises a step of filtering the respiratory flow rate signal Qr to reduce background noise, e.g. the sound of airflow in the system from the blower 4142.

8.4.3.2.6 Determination of Airway Patency

In one form of the present technology, a central controller 4230 executes one or more algorithms 4327 for the determination of airway patency.

In one form, airway patency algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency algorithm 4327 receives as an input a respiratory flow rate signal Qr, and determines the presence or absence of a cardiogenic signal. The absence of a cardiogenic signal is taken to be an indication of a closed airway.

8.4.3.2.7 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi) + P_0 \quad (1)$$

where:

A is an amplitude,

Φ is the current value of phase;

$\Pi(\Phi)$ is the waveform template value (in the range 0 to 1) at the current value of phase, and $P_0$ is a base pressure.

If the waveform determination algorithm 4322 provides the waveform template $\Pi(\Phi)$ as a lookup table of values indexed by phase $\Phi$ the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen pressure therapy mode in the manner described below.

8.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of gas whose mask pressure Pm at the patient interface 3000 is equal to the treatment pressure Pt.

8.4.3.4 Detection of Fault Conditions

In one form of the present technology, a processor executes one or more methods 4340 for the detection of fault conditions. The fault conditions detected by the one or more methods may include at least one of the following:

Power failure (no power, or insufficient power)

Transducer fault detection

Failure to detect the presence of a component

Operating parameters outside recommended ranges (e.g. pressure, flow, temperature, $PaO_2$)

Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm

Sending a message to an external device

Logging of the incident

8.5 Humidifier

In one form of the present technology there is provided a humidifier 5000 (e.g. as shown in FIG. 5) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

8.6 Breathing Waveforms

FIG. 6A shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, −0.5 L/s. The total duration of the breath, Ttot, is about 4 s. The person typically breathes at a respiratory rate of about 15 breaths per minute (bpm), with ventilation, Vent, about 7.5 L/minute. A typical duty cycle, the ratio of Ti to Ttot, is about 40%.

FIG. 6C shows an example of respiratory flow rate during Cheyne-Stokes respiration, along with various quantities calculated therefrom. The top tracing 6000 is respiratory flow rate signal Qr, showing alternating hyperpneas 6010 and apneas 6020 characteristic of CSR. The second tracing 6030 is the absolute value of the respiratory flow rate Qr. The tracing 6040 is a measure of ventilation Vent equal to the tracing 6030 low-pass filtered with a time constant of a few breaths. The tracing 6050 is the typical recent ventilation Vtyp, calculated as the measure of ventilation Vent low-pass filtered with a time constant of one hundred seconds, and the tracing 6060 is the target ventilation Vtgt, set to the typical recent ventilation Vtyp multiplied by 0.9. The measure of ventilation Vent (tracing 6040) exceeds the target ventilation Vtgt (tracing 6060) during the hyperpneas of the CSR, e.g. at the point 6070, and falls below the target ventilation Vtgt during the hypopneas, e.g. at the point 6080.

8.7 Respiratory Pressure Therapy Modes

Various respiratory pressure therapy modes may be implemented by the RPT device 4000 depending on the values of the parameters A and $P_0$ in the treatment pressure equation (1) used by the therapy parameter determination algorithm 4329 in one form of the present technology.

8.7.1 CPAP Therapy

In some implementations of this form of the present technology, the amplitude A is identically zero, so the treatment pressure Pt is identically equal to the base pressure $P_0$ throughout the breathing cycle. Such implementations are generally grouped under the heading of CPAP therapy. In such implementations, there is no need for the therapy engine module 4320 to determine phase $\Phi$ or the waveform template $\Pi(\Phi)$.

In CPAP therapy modes, the base pressure $P_0$ may be a constant value that is hard-coded or manually entered to the RPT device 4000. This alternative is sometimes referred to as constant CPAP therapy. The constant value for the base pressure $P_0$ may be selected for a given patient via a process known as titration.

During titration, a clinician typically adjusts the treatment pressure Pt in response to observations of flow limitation, apnea, hypopnea, patency, and snore during a titration session. The titrated base pressure $P_0$ may be then computed as a statistical summary of the treatment pressure Pt during the titration session.

Alternatively, the therapy parameter determination algorithm 4329 may frequently or continuously compute the base pressure $P_0$ during therapy. This alternative is sometimes referred to as APAP therapy. In one such implementation, the therapy parameter determination algorithm 4329 continuously computes the base pressure $P_0$ as a function of indices or measures of sleep disordered breathing returned by the respective algorithms in the therapy engine module 4320, such as one or more of flow limitation, apnea, hypopnea, patency, and snore. Because the continuous computation of the base pressure $P_0$ in this manner resembles the manual adjustment of the treatment pressure Pt by a clinician during titration of constant CPAP therapy, APAP therapy is also sometimes referred to as auto-titrating CPAP.

FIG. 4E is a flow chart illustrating a method 4500 carried out by the central controller 4230 to frequently or continuously compute the base pressure $P_0$ in response to indices or measures of sleep disordered breathing. The frequency at which calculations are done may vary and will depend on various factors such processor or controller speed, the amount of data being collected or measured by a sensor, the different activities a controller may be tasked with, etc. Thus, while a controller may make a computation during every clock, computations need not be done at each available opportunity or continuously. The method 4500 may be used as part of an APAP therapy implementation of the therapy parameter determination algorithm 4329.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 $cmH_2O$ and 25 $cmH_2O$ respectively. In other implementations, the pressure increment $\Delta P$ can be as low as 0.1 $cmH_2O$ and as high as 3 $cmH_2O$, or as low as 0.5 $cmH_2O$ and as high as 2 $cmH_2O$. In other implementations, the maximum treatment pressure Pmax can be as low as 15 $cmH_2O$ and as high as 35 $cmH_2O$, or as low as 20 $cmH_2O$ and as high as 30 $cmH_2O$. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant $\tau$ of the exponential decrease of $P_0$ is 60 minutes, and the minimum treatment pressure Pmin is 4 $cmH_2O$. In other implementations, the time constant $\tau$ could be as low as 1 minute and as high as 300 minutes, or as low as 5 minutes and as high as 180 minutes. In other implementations, the minimum treatment pressure Pmin can be as low as 0 $cmH_2O$ and as high as 8 $cmH_2O$, or as low as 2 $cmH_2O$ and as high as 6 $cmH_2O$. Alternatively, the decrement in $P_0$ could be predetermined, so the decrease in $P_0$ to the minimum treatment pressure Pmin in the absence of any detected events is linear.

Although primarily used to treat OSA, APAP therapy may also be used to treat CSR. In one such form of the present technology, the therapy parameter determination algorithm 4329 frequently or continuously computes the base pressure $P_0$ based on the relative values of the measure of ventilation Vent provided by the ventilation determination algorithm 4311 and the target ventilation Vtgt provided by the target ventilation determination algorithm 4313. The aim of the adjustment of the base pressure $P_0$ is to manipulate the Functional Residual Capacity (FRC) of the patient's lungs. Increasing the FRC increases the amount of air stored in the lungs, which tends to reduce the amount of gas exchange, and thus reduces the instability that leads to CSR.

There are many possible control strategies that may be used to implement this form of the present technology. In one control strategy, known as proportional control, the therapy parameter determination algorithm 4329 modulates the base pressure $P_0$ around a default value proportionally to the difference between the measure of ventilation Vent and the target ventilation Vtgt. The modulation of the base pressure $P_0$ may be in either sense, depending on the pathophysiology of the patient 1000. That is, the therapy parameter determination algorithm 4329 may increase the base pressure $P_0$ when the measure of ventilation Vent exceeds the target ventilation Vtgt, possibly indicating a hyperpnea of a CSR cycle, and decrease the base pressure $P_0$ when the measure of ventilation Vent falls below the target ventilation Vtgt, possibly indicating a hypopnea of a CSR cycle. Alternatively, the therapy parameter determination algorithm 4329 may decrease the base pressure $P_0$ when the measure of ventilation Vent exceeds the target ventilation Vtgt, and increase the base pressure $P_0$ when the measure of ventilation Vent falls below the target ventilation Vtgt.

Other control strategies that may be used to implement this form of the present technology include proportional-integral (PI) control, proportional-differential (PD) control, proportional-integral-differential (PID) control, and discrete control.

In other forms of the present technology, the base pressure $P_0$ of CPAP therapy may be adjusted to treat CSR independently of the measure of ventilation Vent and the target ventilation Vtgt. In one implementation of such a form, the base pressure $P_0$ is generally maintained at a default value (whether constant or continuously computed to treat OSA, as described above). The base pressure $P_0$ is periodically (for example, at intervals of ten to fifteen minutes) elevated to a high level (for example 20 $cmH_2O$) for a short time (for example, thirty to sixty seconds). The high level is high enough, and the short time is long enough, to inflate the lungs, which by the Hering-Breuer reflex induces a central apnea lasting up to a minute. These central apneas cause the patient's average $CO_2$ level to rise. Over time, the patient's respiratory system adapts to this increase by either increasing the threshold of the chemoreceptors or reducing the "plant gain" of the patient's respiratory system. In either case, these adaptations mean that CSR cycles are less likely to occur.

8.7.2 Pressure Support Ventilation Therapy

In other implementations of the form of the present technology in which the therapy parameter determination algorithm 4329 uses equation (1) to determine the treatment pressure Pt, the value of amplitude A in equation (1) may be positive and large enough that the RPT device 4000 does some or all of the work of breathing of the patient 1000. In such forms, known as pressure support ventilation therapy, the amplitude A is referred to as the pressure support, or swing.

By determining the treatment pressure Pt using equation (1) with positive pressure support A, the therapy parameter determination algorithm 4329 oscillates the treatment pressure Pt between two values in synchrony with the spontaneous respiratory effort of the patient 1000. That is, based on the typical waveform templates $\Pi(\Phi)$ described above, the therapy parameter determination algorithm 4329 increases the treatment pressure Pt to $P_0+A$ (a value known as the IPAP) at the start of, or during, or inspiration and decreases the treatment pressure Pt to the base pressure $P_0$ (a value known as the EPAP) at the start of, or during, expiration.

In some forms of pressure support ventilation therapy, known as fixed pressure support ventilation therapy, the pressure support A is fixed at a predetermined value, e.g. 10 cmH$_2$O. The predetermined pressure support value is a setting of the RPT device 4000, and may be set for example by hard-coding during configuration of the RPT device 4000 or by manual entry through the input device 4220.

In some forms of pressure support ventilation therapy, known as servo-ventilation, the therapy parameter determination algorithm 4329 frequently or continuously computes the pressure support A so as to bring the current measure of ventilation Vent provided by the ventilation determination algorithm 4311 towards the target ventilation Vtgt provided by the target ventilation determination algorithm 4313. In a form of servo-ventilation known as adaptive servo-ventilation (ASV), which has been used to treat CSR, the target ventilation determination algorithm 4313 computes the target ventilation Vtgt from the typical recent ventilation Vtyp, as described above. The frequency or continuous nature of the computations may vary as discussed above.

In various forms of servo-ventilation, the therapy parameter determination algorithm 4329 applies various control methodologies to frequently or continuously compute the pressure support A so as to bring the current measure of ventilation Vent towards the target ventilation Vtgt. One such control methodology is Proportional-Integral (PI) control. In one implementation of PI control, suitable for ASV modes in which the target ventilation Vtgt is set to slightly less than the typical recent ventilation Vtyp, the pressure support A is computed as:

$$A = G\!\int(\text{Vent}-\text{Vtgt})dt \qquad (2)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH$_2$O/(L/min)/sec. Alternatively, the gain G may be varied between therapy sessions, starting small and increasing from session to session until a value that substantially eliminates CSR is reached. Conventional means for retrospectively analyzing the parameters of a therapy session to assess the severity of CSR during the therapy session may be employed in such implementations. In yet other implementations, the gain G may vary depending on the difference between the current measure of ventilation Vent and the target ventilation Vtgt.

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, as during the "waning" portion of a Cheyne-Stokes respiration cycle (see point 6080 in FIG. 6C). At such a point, the pressure support A starts increasing, only falling back to Amin when Vent exceeds Vtgt once again.

The pressure support limits Amin and Amax may be settings of the RPT device 4000, set for example by hard-coding during configuration of the RPT device 4000 or by manual entry through the input device 4220. A minimum pressure support Amin of 3 cmH$_2$O is of the order of 50% of the pressure support required to perform all the work of breathing of a typical patient in the steady state. A maximum pressure support Amax of 12 cmH$_2$O is approximately double the pressure support required to perform all the work of breathing of a typical patient, and therefore sufficient to support the patient's breathing if they cease making any efforts, but less than a value that would be uncomfortable or dangerous.

In an alternative implementation of PI control, suitable for ASV modes in which a target ventilation Vtgt is set to slightly greater than the typical recent ventilation Vtyp, the pressure support A is computed as $$A = A\text{max} + G\!\int(\text{Vent}-\text{Vtgt})dt \qquad (3)$$

and clipped to the range [Amin, Amax]. The gain G is fixed at a predetermined negative value, such as −0.4 cmH$_2$O/(L/min)/sec. In this alternative implementation of PI control, the pressure support A sits by default at the maximum pressure support Amax until the measure of current ventilation Vent rises above the target ventilation Vtgt, as during the "waxing" portion of a Cheyne-Stokes respiration cycle (see point 6070 in FIG. 6C). At such a point, according to equation (3), the pressure support A starts decreasing, only rising back to Amax when Vtgt exceeds Vent once again. In this alternative implementation of PI control, the upper limit Amax may be set somewhat lower than the upper limit Amax in PI control according to equation (2), e.g. to 8 cmH$_2$O.

Other servo-ventilation control methodologies that may be applied by the therapy parameter determination algorithm 4329 to determine the pressure support A include proportional (P), proportional-differential (PD), and proportional-integral-differential (PID).

Another servo-ventilation control methodology returns a pressure support A that is one of a discrete set of predetermined values. In one implementation of such a methodology, known as "discrete control", the pressure support A is increased from a default low level $A_1$ (e.g. 3 cmH$_2$O) to a higher level $A_2$ (e.g. 8 cmH$_2$O) if the measure of ventilation Vent falls below a first threshold, and returns to the low level $A_1$ if the measure of ventilation Vent rises above a second threshold. The second threshold may be set higher than the first threshold to provide some hysteresis to stabilize the discrete control. The first and second thresholds could be predetermined, or made dependent on the current patient state, e.g. as functions of the typical recent ventilation Vtyp. In other, more complicated implementations of discrete control, more thresholds and more corresponding discrete pressure support levels may be used.

Another form of servo-ventilation is referred to as "anti-ventilation". Under anti-ventilation, the therapy parameter determination algorithm 4329 computes the treatment pressure Pt according to equation (1), i.e. to oscillate in phase with the patient's spontaneous respiratory efforts, as long as the measure of ventilation Vent is less than a first threshold. If the measure of ventilation Vent exceeds the first threshold, the therapy parameter determination algorithm 4329 computes the treatment pressure Pt according to equation (1)

with the phase Φ shifted by 0.5 revolutions, i.e. to oscillate in antiphase with the patient's spontaneous respiratory efforts. The effect of this half-cycle phase shift is to reverse the usual sense of pressure support in which the treatment pressure Pt is higher during the inspiratory portion of the breathing cycle, and lower during the expiratory portion. With the phase shifted by 0.5 revolutions in equation (1), the treatment pressure Pt is lower during the inspiratory portions of the breathing cycle, and higher during the expiratory portions (hence the name "anti-ventilation"). This reversal effectively counteracts the increase in respiratory effort causing the increase in ventilation. The "anti-ventilation" continues until the measure of ventilation falls below a second threshold, at which point the therapy parameter determination algorithm 4329 returns to computing the treatment pressure Pt according to equation (1) without any phase shift. The second threshold may be set less than the first threshold to provide some hysteresis to stabilize the anti-ventilation control. The first and second thresholds could be predetermined, or dependent on the current patient state, e.g. as functions of the typical recent ventilation Vtyp. The pressure support A may be set to a constant, moderate value, e.g. 4 $cmH_2O$, for both senses of ventilation. Alternatively, anti-ventilation could be combined with other forms of servo-control, as described above, in which the amplitude A is continuously computed as a function of the measure of ventilation Vent.

8.8 Glossary

For the purposes of the present disclosure, in certain forms of the present technology, one or more of the following definitions may apply. In other forms of the present technology, alternative definitions may apply.

8.8.1 General

Air: In certain forms of the present technology, air may be taken to mean atmospheric air, and in other forms of the present technology air may be taken to mean some other combination of breathable gases, e.g. atmospheric air enriched with oxygen.

Respiratory Pressure Therapy (RPT): The delivery of a supply of air to the airways at a treatment pressure that is typically positive with respect to atmosphere.

Continuous Positive Airway Pressure (CPAP) therapy: Respiratory pressure therapy in which the treatment pressure is approximately constant through a breathing cycle of a patient. In some forms, the pressure at the entrance to the airways will be slightly higher during exhalation, and slightly lower during inhalation. In some forms, the pressure will vary between different breathing cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

8.8.2 Aspects of the Breathing Cycle

Apnea: According to some definitions, an apnea is said to have occurred when respiratory flow rate falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate, or respiratory rate (Rs): The rate of spontaneous respiration of a patient, usually measured in breaths per minute.

Duty cycle: The ratio of inhalation time, Ti to total breath duration, Ttot.

Effort (breathing): The work done by a spontaneously breathing person attempting to breathe.

Expiratory portion of a breathing cycle: The period from the start of expiratory flow to the start of inspiratory flow.

Flow limitation: The state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: A reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow rate (Qpeak): The maximum value of flow during the inspiratory portion of the respiratory flow rate waveform.

Respiratory flow/airflow rate, patient flow/airflow rate (Qr): These synonymous terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

Inhalation Time (Ti): The duration of the inspiratory portion of the respiratory flow rate waveform.

Exhalation Time (Te): The duration of the expiratory portion of the respiratory flow rate waveform.

(total) Time, or breath duration (Ttot): The total duration between the start of the inspiratory portion of one respiratory flow rate waveform and the start of the inspiratory portion of the following respiratory flow rate waveform.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

8.8.3 RPT Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow rate will be given the symbol Q. 'Flow rate' is sometimes shortened to simply 'flow'. Total flow rate, Qt, is the flow of air leaving the RPT device. Vent flow rate, Qv, is the flow of air leaving a vent to allow washout of exhaled gases. Leak flow rate, Ql, is the flow rate of unintentional leak from a patient interface system.

Respiratory flow rate, Qr, is the flow of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface (mask pressure) is given the symbol Pm, while the treatment pressure, which represents a target value to be achieved by the mask pressure Pm at the current instant of time, is given the symbol Pt.

8.8.4 Terms for Ventilators

Adaptive Servo-Ventilator (ASV): A servo-ventilator that has a changeable rather than a fixed target ventilation. The changeable target ventilation may be learned from some characteristic of the patient, for example, a respiratory characteristic of the patient.

Backup rate: A parameter of a ventilator that establishes the respiratory rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Servo-assistance: Pressure support minus minimum pressure support.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the inspiratory portion of the breathing cycle by the patient's efforts.

Typical recent ventilation: The typical recent ventilation Vtyp is the value around which recent measures of ventilation over some predetermined timescale tend to cluster, that is, a measure of the central tendency of the measures of ventilation over recent history.

Ventilator: A mechanical device that provides pressure support to a patient to perform some or all of the work of breathing.

8.8.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.9 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

8.10 Reference Label List patient 1000
bed partner 1100
patient interface 3000
seal-forming structure 3100
plenum chamber 3200
structure 3300
vent 3400
connection port 3600
forehead support 3700
RPT device 4000
external housing 4010
portion 4012
portion 4014
panel 4015
chassis 4016
handle 4018
pneumatic block 4020
pneumatic components 4100
air filters 4110
air inlet filter 4112
air outlet filter 4114
mufflers 4120
inlet muffler 4122
outlet muffler 4124
pressure generator 4140
blower 4142
brushless DC motor 4144
anti-spill back valve 4160
air delivery circuit 4170
supplemental oxygen 4180
electrical components 4200

PCBA 4202
power supply 4210
input devices 4220
central controller 4230
clock 4232
therapy device controller 4240
protection circuit 4250
memory 4260
transducers 4270
pressure transducer 4272
flow transducer 4274
motor speed transducer 4276
data communication interface 4280
remote external communication network 4282
local external communication network 4284
remote external device 4286
local external device 4288
output device 4290
display driver 4292
display 4294
algorithms 4300
pre-processing module 4310
ventilation determination algorithm 4311
pressure compensation algorithm 4312
target ventilation determination algorithm 4313
vent flow rate estimation algorithm 4314
leak flow rate estimation algorithm 4316
respiratory flow estimation algorithm 4317
respiratory rate estimation algorithm 4318
backup rate determination algorithm 4319
therapy engine module 4320
phase determination algorithm 4321
waveform determination algorithm 4322
flow limitation determination algorithm 4324
apnea/hypopnea detection algorithm 4325
snore detection algorithm 4326
airway patency algorithm 4327
therapy parameter determination algorithm 4329
therapy control module 4330
method 4340
method 4500
step 4520
step 4530
step 4540
step 4550
step 4560
humidifier 5000
tracing 6000
hyperpneas 6010
apneas 6020
tracing 6030
tracing 6040
tracing 6050
tracing 6060
point 6070
point 6080

The invention claimed is:

1. An apparatus for treating a respiratory disorder in a patient, the apparatus comprising:
a pressure generator configured to generate a supply of air at a positive pressure to an airway of the patient;
a sensor configured to generate data representing a property of the supply of air; and
a controller configured to:
control the pressure generator to generate the supply of air at a positive treatment pressure that oscillates in synchrony with the patient's spontaneous respiratory efforts, wherein an amplitude of oscillation of the positive treatment pressure is a pressure support;
compute a measure indicative of ventilation of the patient from the sensor data;
compute the pressure support so as to bring the measure indicative of ventilation towards a target ventilation that is dependent on the measure indicative of ventilation;
determine periods that servo-assistance is below a threshold, wherein servo-assistance is the pressure support minus a minimum pressure support and the pressure support is a number that is indicative of an increase in pressure during ventilator inspiration over pressure during ventilator expiration; and
compute a spontaneous respiratory rate using sensor data particular to the determined periods, wherein the spontaneous respiratory rate is repeatedly updated to new spontaneous respiratory rates, wherein each of the new spontaneous rates is determined with a period of estimation, and wherein the period of estimation progressively increases up to a maximum duration; and
control the pressure generator to deliver backup breaths at a backup rate in the absence of significant spontaneous respiratory efforts from the patient,
wherein the backup rate increases from a spontaneous backup rate to a sustained timed backup rate; and wherein the controller is configured to compute the backup rate as a function of the computed spontaneous respiratory rate and a constant.

2. The apparatus according to claim 1, wherein the spontaneous backup rate is a fraction of the sustained timed backup rate.

3. The apparatus according to claim 1, wherein the controller is further configured to:
estimate the spontaneous respiratory rate of the patient, and
set the sustained timed backup rate dependent on the estimated spontaneous respiratory rate.

4. The apparatus according to claim 3, wherein the estimating comprises computing a reciprocal of a measure of central tendency of breath duration over one or more periods when the patient is breathing spontaneously.

5. The apparatus according to claim 4, wherein the periods are periods of asleep breathing.

6. The apparatus according to claim 4, wherein the periods are periods when servo-assistance is low.

7. The apparatus according to claim 4, wherein the measure of central tendency is one of:
a mean;
a median; and
a trimmed mean.

8. The apparatus according to claim 4, wherein the estimating comprises performing interval filtering before computing the measure of central tendency.

9. The apparatus according to claim 4, wherein the estimating comprises excluding breaths that are not part of a sequence of predetermined length of spontaneous breaths from the measure of central tendency.

10. The apparatus according to claim 4, wherein the estimating comprises excluding early and late breaths of a sequence of spontaneous breaths from the measure of central tendency.

11. The apparatus according to claim 4, wherein the estimating comprises:
computing an estimate of the spontaneous respiratory rate over an initial period of estimation, and updating the estimate of the spontaneous respiratory rate using a period of estimation that is longer than the initial period of estimation.

12. The apparatus according to claim 4, wherein the estimating further comprises applying a low-pass filter to the computed measure of central tendency.

13. The apparatus according to claim 1, wherein the increase of the backup rate is according to a predetermined profile such that the backup rate reaches the sustained timed backup rate after a predetermined interval.

14. The apparatus according to claim 13, wherein the predetermined profile is a continuous linear profile.

15. The apparatus according to claim 13, wherein the predetermined interval is a function of adequacy of current ventilation.

16. The apparatus according to claim 1, wherein controlling the pressure generator to deliver backup breaths at the backup rate comprises:
   detecting a start of inhalation due to spontaneous respiratory effort; and
   triggering the pressure generator upon not detecting the start of inhalation within a period of time after a last trigger instant whose duration is equal to a reciprocal of the backup rate.

17. The apparatus according to claim 1, wherein controlling the pressure generator to generate the supply of air at the positive treatment pressure that oscillates in synchrony with the patient's spontaneous respiratory efforts comprises:
   determining a phase of a current breathing cycle of the patient, and
   increasing the positive treatment pressure upon the phase indicating a start of inspiration and decreasing the positive treatment pressure upon the phase indicating a start of expiration.

18. The apparatus according to claim 17, wherein the phase is a discrete variable.

19. The apparatus according to claim 17, wherein the phase is a continuous variable.

20. The apparatus according to claim 1, wherein the controller is further configured to compute the target ventilation as a proportion of less than a typical recent value of the measure indicative of ventilation.

21. The apparatus according to claim 1, wherein continuously computing the pressure support uses a control strategy drawn from a group consisting of: proportional control, proportional-integral control, proportional-differential control, and proportional-integral-differential control.

22. The apparatus according to claim 1, wherein computing the pressure support uses discrete control.

23. The apparatus according to claim 1, wherein the measure indicative of ventilation is half an absolute value of respiratory flow rate.

24. The apparatus according to claim 23, further comprising filtering the absolute value of respiratory flow rate by a low-pass filter.

25. The apparatus according to claim 1, wherein the measure indicative of ventilation is an estimate of gross alveolar ventilation.

26. The apparatus according to claim 1, wherein the measure indicative of ventilation is proportional to an actual ventilation of the patient.

27. The apparatus according to claim 26, wherein the measure indicative of ventilation is a peak respiratory flow rate over an inspiratory portion of a breathing cycle.

28. The apparatus according to claim 1, wherein the measure indicative of ventilation is oxygen saturation.

29. The apparatus according to claim 1, wherein the treatment pressure oscillates in phase with the patient's spontaneous respiratory efforts when the measure indicative of ventilation is less than a first threshold, and in antiphase with the patient's spontaneous respiratory efforts when the measure indicative of ventilation is greater than a second threshold.

30. The apparatus according to claim 29, wherein the second threshold is less than the first threshold.

31. The apparatus according to claim 29, wherein the first and second thresholds are functions of a typical recent value of the measure indicative of ventilation.

32. A method of treating a respiratory disorder in a patient, the method comprising:
   controlling a pressure generator to generate a supply of air at a positive treatment pressure to an airway of the patient, wherein the positive treatment pressure oscillates in synchrony with the patient's spontaneous respiratory efforts, wherein an amplitude of oscillation of the positive treatment pressure is a pressure support;
   computing a measure indicative of ventilation of the patient from data representing a property of the supply of air;
   computing the pressure support so as to bring the measure indicative of ventilation towards a target ventilation that is dependent on the measure indicative of ventilation;
   determining periods during the supply of air when servo-assistance is below a threshold;
   computing a spontaneous respiratory rate using sensor data from the determined periods, wherein the spontaneous respiratory rate is repeatedly updated to new spontaneous respiratory rates, wherein each of the new spontaneous rates is determined with a period of estimation, and wherein the period of estimation progressively increases up to a maximum duration; and
   controlling the pressure generator to deliver backup breaths at a backup rate in the absence of significant spontaneous respiratory efforts from the patient, the backup rate being derived as a function of the computed spontaneous respiratory rate;
   wherein the backup rate increases from a spontaneous backup rate to a sustained timed backup rate.

33. A computer-readable memory storage apparatus having computer-executable instructions encoded thereon which, when executed by a processor, cause the processor to perform the method according to claim 32.

34. The method of claim 32 further comprising computing the backup rate as a function of the spontaneous respiratory rate and a constant.

* * * * *